(12) United States Patent
Yamaji et al.

(10) Patent No.: US 11,166,664 B2
(45) Date of Patent: Nov. 9, 2021

(54) INFORMATION PROCESSING DEVICE, INFORMATION PROCESSING METHOD, AND RECORDING MEDIUM

(71) Applicant: FUJITSU LIMITED, Kawasaki (JP)

(72) Inventors: Takayuki Yamaji, Yokohama (JP); Hirohisa Naito, Fuchu (JP)

(73) Assignee: FUJITSU LIMITED, Kawasaki (JP)

( * ) Notice: Subject to any disclaimer, the term of this patent is extended or adjusted under 35 U.S.C. 154(b) by 418 days.

(21) Appl. No.: 16/055,258

(22) Filed: Aug. 6, 2018

(65) Prior Publication Data

US 2018/0338717 A1 Nov. 29, 2018

Related U.S. Application Data

(63) Continuation of application No. PCT/JP2016/059829, filed on Mar. 28, 2016.

(51) Int. Cl.
*A61B 5/00* (2006.01)
*A61B 5/11* (2006.01)
*A61B 5/16* (2006.01)

(52) U.S. Cl.
CPC .......... *A61B 5/4815* (2013.01); *A61B 5/1115* (2013.01); *A61B 5/1118* (2013.01);
(Continued)

(58) Field of Classification Search
CPC ... A61B 5/4812; A61B 5/4815; A61B 5/1115; A61B 5/1118; A61B 5/16; A61B 5/0022
(Continued)

(56) References Cited

U.S. PATENT DOCUMENTS 8,852,127 B2 * 10/2014 Bell .................... A61B 5/11
600/587
9,962,120 B2 * 5/2018 Aoyama ................ A61B 5/486
(Continued)

FOREIGN PATENT DOCUMENTS

JP 2004-358235 A 12/2004
JP 2006-129887 A 5/2006
(Continued)

OTHER PUBLICATIONS

International Search Report and Written Opinion w/English translation dated Jun. 28, 2016, issued in counterpart International Application No. PCT/JP2016/059829 (8 pages).
(Continued)

*Primary Examiner* — David J. McCrosky
*Assistant Examiner* — Chanel J Jhin
(74) *Attorney, Agent, or Firm* — Westerman, Hattori, Daniels & Adrian, LLP

(57) ABSTRACT

An information processing device includes: a processor configured to: acquire time series data relating to at least one of acceleration, amounts of activity of a subject whose sleep is to be evaluated, and body positions of the subject, the time series data being measured by a sensor device that the subject wears; obtain a result of evaluation by analyzing a state of the subject that relates to sleep in each of three sections which are obtained by dividing an evaluation period from a getting-into-bed time point or a first onset-of-sleep time point after getting into bed that is specified by the time-series data until a getting-out-of-bed time point or a last waking time point before getting out of bed; and output the result of evaluation so as to identify that the result corresponds to any one of the three sections.

4 Claims, 22 Drawing Sheets

(52) U.S. Cl.
CPC .............. *A61B 5/16* (2013.01); *A61B 5/4812* (2013.01); *A61B 5/0022* (2013.01)

(58) Field of Classification Search
USPC ........................................................ 600/595
See application file for complete search history.

(56) References Cited

U.S. PATENT DOCUMENTS

| | | | |
|---|---|---|---|
| 9,968,293 B1* | 5/2018 | Kahn | A61B 5/11 |
| 10,575,751 B2* | 3/2020 | Abeyratne | A61B 5/7264 |
| 2004/0230398 A1 | 11/2004 | Okada et al. | |
| 2006/0094938 A1 | 5/2006 | Shimada et al. | |
| 2008/0004811 A1 | 1/2008 | Suzuki et al. | |
| 2011/0092831 A1* | 4/2011 | Herscovici-Cohen | A61B 5/1073 600/500 |
| 2013/0324889 A1 | 12/2013 | Togo et al. | |
| 2014/0005503 A1* | 1/2014 | Ni | A61N 1/36542 600/301 |
| 2014/0088378 A1* | 3/2014 | Muzet | A61B 5/1123 600/301 |
| 2015/0224017 A1* | 8/2015 | Graindorge | A61H 23/00 601/46 |
| 2015/0230750 A1* | 8/2015 | McDarby | A61B 5/0816 600/407 |
| 2016/0100792 A1* | 4/2016 | Ding | A61B 5/4812 600/301 |
| 2016/0151603 A1* | 6/2016 | Shouldice | A61M 21/02 600/28 |
| 2016/0296164 A1* | 10/2016 | Garcia Molina | A61B 5/0476 |

FOREIGN PATENT DOCUMENTS

| | | |
|---|---|---|
| JP | 2008-6005 A | 1/2008 |
| JP | 2012-187349 A | 10/2012 |
| JP | 2015-97713 A | 5/2015 |
| JP | 2015-223215 A | 12/2015 |

OTHER PUBLICATIONS

Office Action dated Aug. 21, 2020, issued in counterpart CN Application No. 201680083217.0, with English translation (22 pages).

* cited by examiner

FIG.4

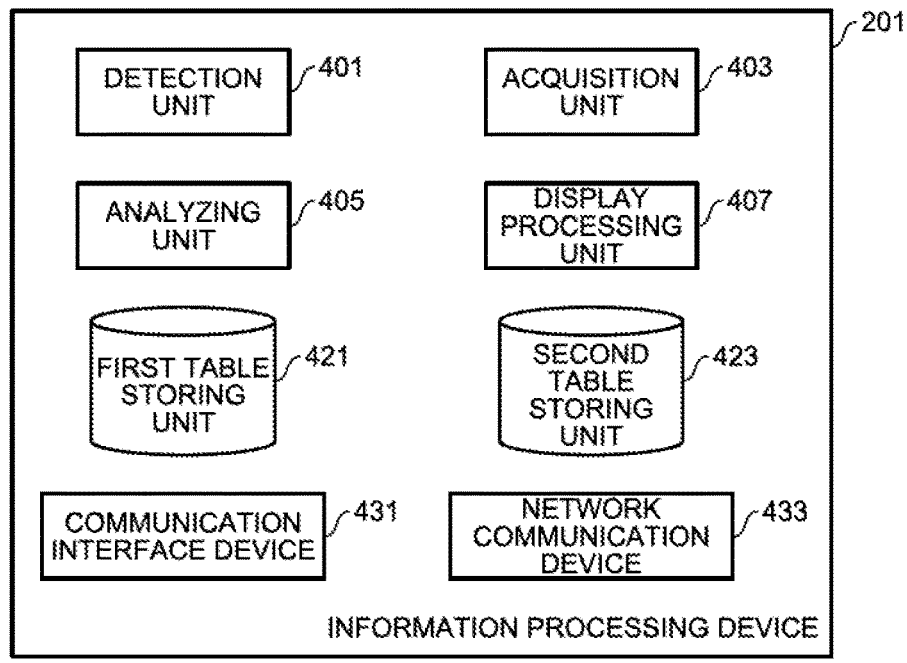

INFORMATION PROCESSING DEVICE

FIG.5

| DATE AND TIME | ACCELERATION | AMOUNT OF ACTIVITY | BODY POSITION | EVENT | STATE OF USER |
|---|---|---|---|---|---|
| ⋮ | ⋮ | ⋮ | ⋮ | ⋮ | ⋮ |
| 2016/1/10 22:20 | $A_{670}$ | $B_{670}$ | PRONE | NON | AWAKE STATE |
| 2016/1/10 22:22 | $A_{671}$ | $B_{671}$ | PRONE | NON | AWAKE STATE |
| 2016/1/10 22:24 | $A_{672}$ | $B_{672}$ | PRONE | NON | AWAKE STATE |
| 2016/1/10 22:26 | $A_{673}$ | $B_{673}$ | PRONE | NON | AWAKE STATE |
| 2016/1/10 22:28 | $A_{674}$ | $B_{674}$ | SUPINE | GETTING INTO BED | AWAKE STATE |
| 2016/1/10 22:30 | $A_{675}$ | $B_{675}$ | SUPINE | NON | AWAKE STATE |
| 2016/1/10 23:32 | $A_{676}$ | $B_{676}$ | SUPINE | ONSET OF SLEEP | SLEEP STATE |
| 2016/1/10 23:34 | $A_{677}$ | $B_{677}$ | SUPINE | NON | SLEEP STATE |
| 2016/1/10 23:36 | $A_{678}$ | $B_{678}$ | SUPINE | NON | SLEEP STATE |
| ⋮ | ⋮ | ⋮ | ⋮ | ⋮ | ⋮ |
| 2016/1/11 6:18 | $A_{909}$ | $B_{909}$ | LATERAL | NON | SLEEP STATE |
| 2016/1/11 6:20 | $A_{910}$ | $B_{910}$ | LATERAL | NON | SLEEP STATE |
| 2016/1/11 6:22 | $A_{911}$ | $B_{911}$ | SUPINE | WAKING | AWAKE STATE |
| 2016/1/11 6:24 | $A_{912}$ | $B_{912}$ | SUPINE | NON | AWAKE STATE |
| 2016/1/11 6:26 | $A_{913}$ | $B_{913}$ | PRONE | GETTING OUT OF BED | AWAKE STATE |
| 2016/1/11 6:28 | $A_{914}$ | $B_{914}$ | UPRIGHT | NON | AWAKE STATE |
| 2016/1/11 6:30 | $A_{915}$ | $B_{915}$ | UPRIGHT | NON | AWAKE STATE |
| ⋮ | ⋮ | ⋮ | ⋮ | ⋮ | ⋮ |

| LEVEL TYPE | CONTENT OF EVALUATION |
|---|---|
| FIRST LEVEL | GOOD |
| SECOND LEVEL | SLIGHTLY GOOD |
| THIRD LEVEL | SLIGHTLY BAD |
| FOURTH LEVEL | BAD |
| ⋮ | ⋮ |

FIG.21

| | | |
|---|---|---|
| SLEEP IN FIRST PERIOD IS (ONSET OF SLEEP) | BAD | 301 |
| SLEEP IN SECOND PERIOD IS | SLIGHTLY BAD | 303 |
| SLEEP IN THIRD PERIOD IS (CONTINUITY) | SLIGHTLY GOOD | 305 |
| SLEEP IN FOURTH PERIOD IS | SLIGHTLY GOOD | 2101 |
| SLEEP IN FIFTH PERIOD IS (WAKING) | GOOD | 2103 |
| ENTIRE SLEEP IS | SLIGHTLY GOOD | 307 |

COMMENT

INFORMATION PROCESSING DEVICE, INFORMATION PROCESSING METHOD, AND RECORDING MEDIUM

CROSS-REFERENCE TO RELATED APPLICATION

This application is a continuation application of International Application PCT/JP2016/059829, filed on Mar. 28, 2016 and designating the U.S., the entire contents of which are incorporated herein by reference.

FIELD

The present invention relates to a technology of evaluating a sleep state.

BACKGROUND

A patent document discloses an example where a sleep state is specified based on human biological information and values of evaluation of sleep in an early period and a late period of a sleep period are calculated separately.

When the sleep state in multiple sections is evaluated separately as described above, how the quality of sleep is viewed differs depending on what sections the period is divided into.

Patent Document 1: Japanese Laid-open Patent Publication No. 2015-223215

Patent Document 2: Japanese Laid-open Patent Publication No. 2008-6005

Patent Document 3: Japanese Laid-open Patent Publication No. 2006-129887

SUMMARY

According to an aspect of the embodiments, an information processing device includes: a processor configured to: acquire time series data relating to at least one of acceleration, amounts of activity of a subject whose sleep is to be evaluated, and body positions of the subject, the time series data being measured by a sensor device that the subject wears; obtain a result of evaluation by analyzing a state of the subject that relates to sleep in each of three sections which are obtained by dividing an evaluation period from a getting-into-bed time point or a first onset-of-sleep time point after getting into bed that is specified by the time-series data until a getting-out-of-bed time point or a last waking time point before getting out of bed; and output the result of evaluation so as to identify that the result corresponds to any one of the three sections.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 4 is a diagram illustrating an exemplary module configuration of an information processing device;

FIG. 5 is a diagram representing an exemplary first table;

FIG. 21 is a diagram illustrating an exemplary evaluation screen in a seventh embodiment;

DESCRIPTION OF EMBODIMENTS

First Embodiment

Figure 1:
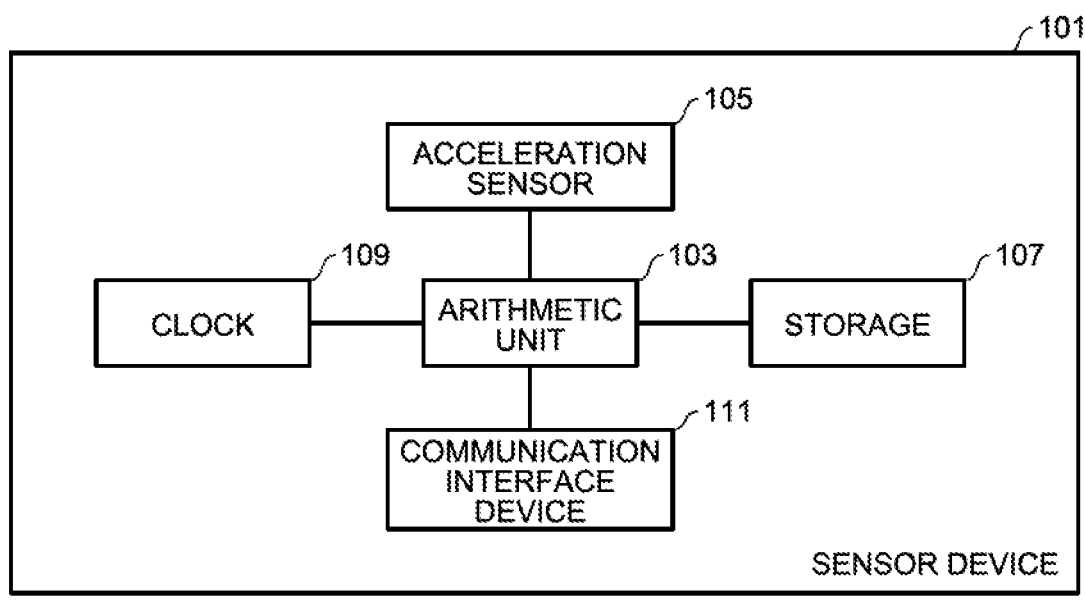
FIG. 1 is a diagram illustrating an exemplary hardware configuration of a sensor device.

FIG. 1 illustrates an exemplary hardware configuration of a sensor device 101. In a state where a user wears the sensor device 101, the sensor device 101 measures acceleration. For example, the sensor device 101 is attached to a belt or pants and is worn in the position of the waist of the user. Note that the sensor device 101 may be worn in another part (such as the head, neck, chest, belly, back, an arm or a leg). Instead of the sensor device 101, a wearable terminal or a mobile phone terminal may be used.

The sensor device 101 includes an arithmetic unit 103, an acceleration sensor 105, a storage 107, a clock 109 and a communication interface device 111. The arithmetic unit 103 performs various types of arithmetic processing. The acceleration sensor 105 measures acceleration. The storage 107 stores various types of data and programs. The clock 109 counts dates. The communication interface device 111 is, for example, a radio integrated circuit (IC) tag or a universal serial bus (USB) interface device. The communication interface device 111 may be another interface device according to near field communication.

The sensor device 101 accumulates acceleration data to which the dates of measurement are added, that is, acceleration time series data. The sensor device 101 outputs the acceleration time series data via the communication interface device 111.

The sensor device 101 may calculate amounts of activity of the user based on the acceleration time series data. The sensor device 101 may output time series data of the calculated amounts of activity via the communication interface device 111. A method of calculating amounts of activity accords with related technologies.

The sensor device 101 may determine body positions of the user based on the acceleration time series data. The sensor device 101 may output time series data about the determined body positions via the communication interface device 111. A method of determining body positions accords with related technologies. Exemplary sensors include a radio-frequency sensor capable of detecting motions of the body, such as the heart or lungs, a sensor capable of detecting pulsation or breathing, a radio-frequency sensor capable of detecting motion of the body itself and an image sensor. In that case, the sensor device 101 may accumulate time series data about all or part of heart rates, breathing rates and body motions and output the time series data via the communication interface device 111. Alternatively, the measured data may be output via the communication interface device 111, another computer may detect heart rates and/or breathing rates and/or body motions and they may be accumulated as time series data.

The user who wears the sensor device 101 (that is, a subject whose sleep is to be evaluated) may be, for example, a railway or vehicle driver. In this example, a manager understands the quality of sleep of a driver whose is going to engage in operations to implement safe operations.

Figure 2A:
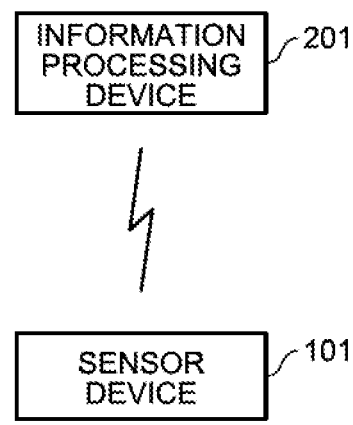
FIG. 2A is a diagram illustrating an exemplary mode of connection.

Thus an information processing device that the manager uses reads the data accumulated in the sensor device 101 and analyzes the data. FIG. 2A illustrates an exemplary mode of connection. In this example, an information processing device 201 reads data directly from the sensor device 101. For example, in a case where the driver is with the manager in a service office, work reduces when data is read directly as described above. Before departure from the service office to a destination, such a mode of connection is assumable.

Figure 2B:
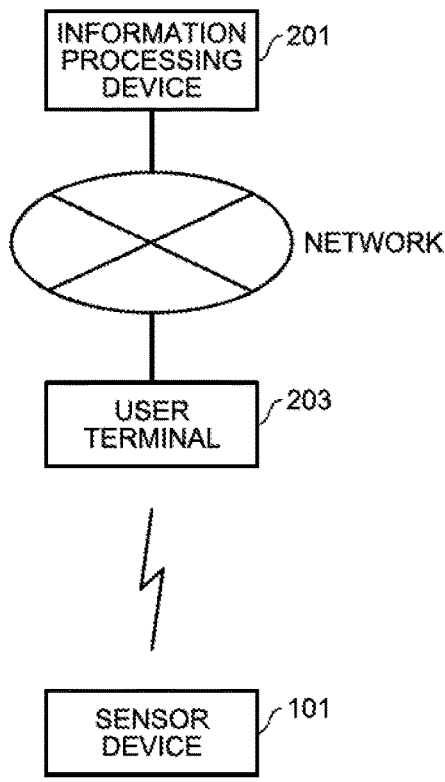
FIG. 2B is a diagram illustrating an exemplary mode of connection.

In a case of a homeward journey from the destination to the service office, a mode of connection like that illustrated in FIG. 2B is assumable. Another mode of connection like that illustrated in FIG. 2B may be possible. A user terminal 203 is caused to temporarily read the data accumulated in the sensor device 101 and the data is transferred from the user terminal 203 to the information processing device 201. Thus the user terminal 203 includes a read device corresponding to the communication interface device 111 of the sensor device 101 and transfers data via a network. The network is, for example, the Internet, a dedicated line or a local area network (LAN). The user terminal 203 is, for example, a mobile phone terminal or a tablet terminal. FIG. 2B illustrates an example where the user terminal 203 and the information processing device 201 are devices different from each other; however, embodiments need not be limited to such a mode of connection. For example, the function of the information processing device 201 to execute the embodiment may be implemented in the user terminal 203.

A user other than drivers, such as a machine operator, a surveillant or a medical representative, may use the sensor device 101.

Figure 3:
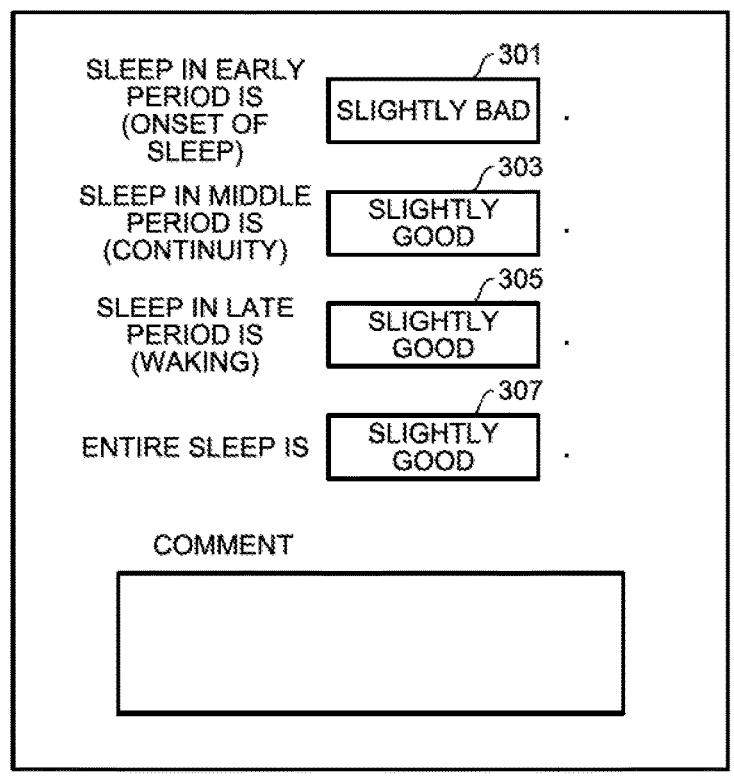
FIG. 3 is a diagram representing an exemplary evaluation screen.

When the information processing device 201 acquires data, analysis is performed automatically and an evaluation screen is displayed. FIG. 3 illustrates an exemplary evaluation screen. As content of evaluation of the quality of sleep of the user, the content of evaluation is represented such that which one of multiple sections obtained by dividing a sleeping time the evaluation is of is identifiable. For example, in addition to the content of the entire evaluation, the content of evaluation of each of three sections divided from an evaluation period is represented. In an area 301 for evaluation of the sleep in a first section, the content of evaluation of the first section, that is, a period relating to onset of sleep, is displayed. In an area 303 for evaluation of the sleep in a second section, the content of evaluation of the middle section, that is, a period relating to continuity of sleep, is displayed. In an area 305 for evaluation of the sleep in a third section, the content of evaluation of the last section, that is, a period relating to waking, is displayed. In an area 307 for overall sleep evaluation, the content of evaluation of the entire evaluation period is displayed.

There are four levels of evaluation in this example. A first level means that the quality of sleep is "good". A second level means that the quality of sleep is "slightly good". A third level means that the quality of sleep is "slightly bad". A fourth level means that the quality of sleep is "bad". Levels of evaluation are not limited to four levels. For example, the levels may be three levels or five levels as long as they are two or more levels.

The manager may write a comment in a comment column. Alternatively, the information processing device 201 may automatically generate a comment. For example, a comment like "The entire sleep is relatively good, but the onset of sleep seemed to be not so good." is displayed. The overview of the present embodiment ends here.

Operations of the information processing device 201 will be described. FIG. 4 illustrates an exemplary module configuration of the information processing device 201. The information processing device 201 includes a detection unit 401, an acquisition unit 403, an analyzing unit 405, display processing unit 407, a first table storing unit 421, a second table storing unit 423, a communication interface device 431, and a network communication device 433.

The detection unit 401 detects the sensor device 101. The acquisition unit 403 executes an acquisition process. The acquisition process will be described below. The analyzing unit 405 executes an analysis process. The analysis process will be described below. The display processing unit 407 is an exemplary output processing unit and executes a display process. The display process will be described below.

The detection unit 401, the acquisition unit 403, the analyzing unit 405 and the display processing unit 407 are implemented using hardware resources (for example, FIG. 26) and a program that causes a processor to execute processes to be described below.

The first table storing unit 421 stores a first table. The first table will be described below using FIG. 5. The second table storing unit 423 stores a second table.

Figure 26:
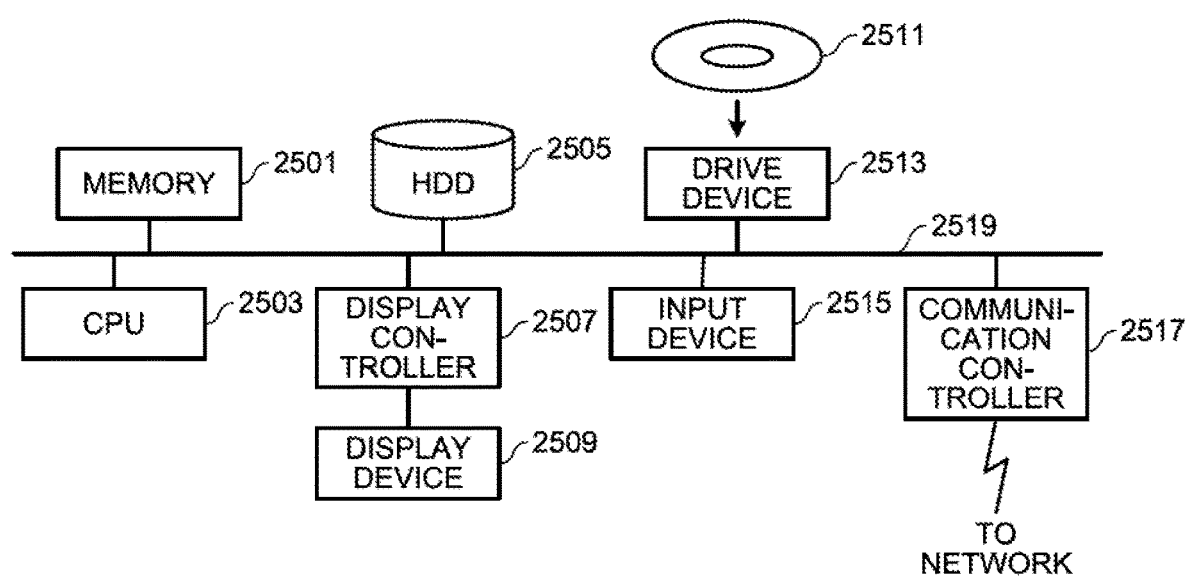
FIG. 26 is a functional block diagram of a computer.

The first table storing unit 421 and the second table storing unit 423 that are aforementioned are implemented using hardware resources (for example, FIG. 26).

The communication interface device 431 implements communication with the communication interface device 111 of the sensor device 101. The communication interface device 431 is, for example, a wireless IC tag read device or a USB interface. The communication interface device 431 may be an interface device according to other near field communication. The network communication device 433 implements communication via the network.

FIG. 5 represents an exemplary first table. The first table of the example has records corresponding to the time points of measurement of acceleration. The records of the first table include a field in which information about dates are stored, a field in which information about acceleration is stored, a field in which information about amounts of activity are stored, a field in which information about body positions are stored, a field in which information about events are stored and a field in which information about states of the user are stored.

A date specifies timing when acceleration is measured. A body position is, for example, a prone position, a supine position, a lateral position or an upright position. An event is any one of getting into bed, onset of sleep and waking. A state of the user is an awake state or a sleep state. Values of dates and acceleration that are stored in the first table are data acquired from the sensor device 101. Values that are acquired from the sensor device 101 or values that are calculated by the information processing device 201 based on the values that are acquired from the sensor device 101 are stored as values of amounts of activity and body positions.

Figures 6, 7:
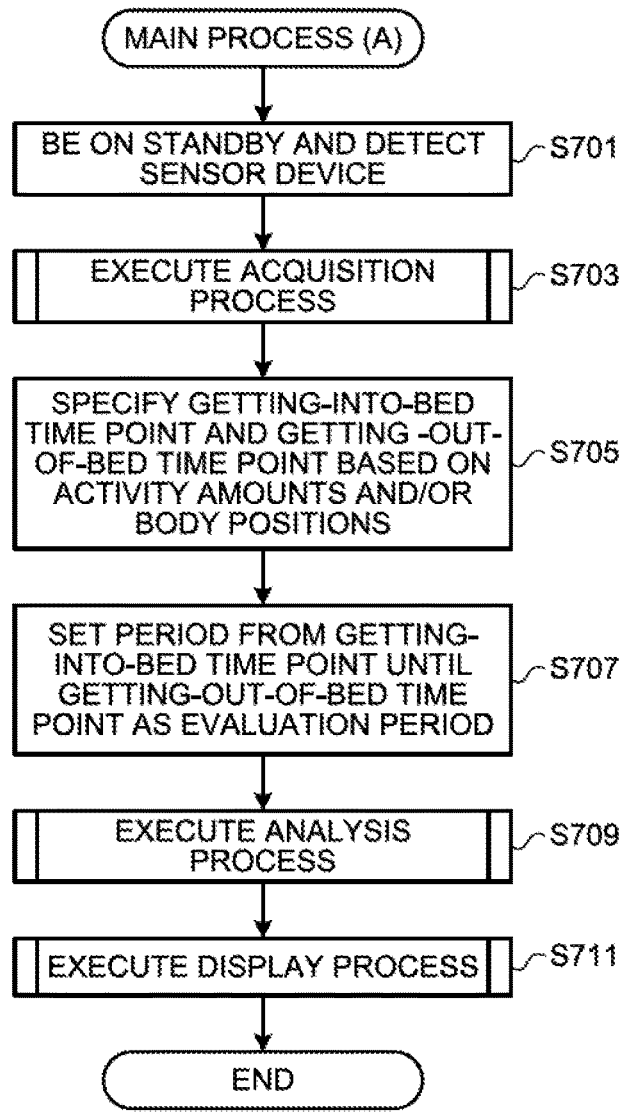
FIG. 6 is a diagram illustrating an exemplary second table.
FIG. 7 is a diagram illustrating a flow of a main process (A)

FIG. 6 represents an exemplary second table. The second table in this example has records corresponding to types of level. The records of the second table include a field for setting types of level and a filed for setting the content of evaluation. A type of level represents a level of evaluation. As described above, the content of evaluation at the first level is "good". Similarly, the content of evaluation at the second level is "slightly good". Similarly, the content of evaluation at the third level is "slightly bad". Similarly, the content of evaluation at the fourth level is "bad". The second table is provided in advance before the process of the present embodiment is executed.

Move on to descriptions of processes performed by the information processing device 201. FIG. 7 illustrates a flow of a main process (A). The detection unit 401 in on standby and detects the sensor device 101 (S701). Specifically, the communication interface device 431 of the information processing device 201 implements communication with the communication interface device 111 of the sensor device 101.

When the sensor device 101 is detected, the acquisition unit 403 executes an acquisition process (S703). In the acquisition process, time series data that is used for analysis is obtained from the sensor device 101.

Figure 8:
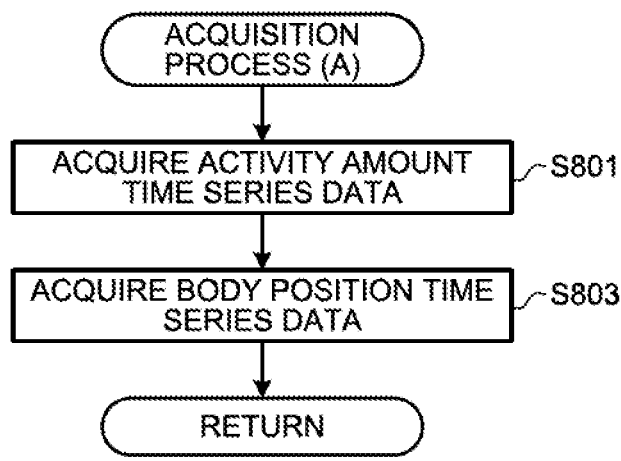
FIG. 8 is a diagram illustrating a flow of an acquisition process (A)

FIG. 8 illustrates a flow of an acquisition process (A). The acquisition process (A) presupposes that the sensor device 101 has calculated amounts of activity and further has determined body positions. The acquisition unit 403 acquires time series data about the amounts of activity via the communication interface device 431 (S801). Furthermore, the acquisition unit 403 acquires the body position time series data via the communication interface device 431 (S803). On ending the acquisition process (A), return to the main process (A) that is the caller process.

When performing analysis based on only the activity amount time series data, the body position time series data need not be acquired. When analysis is performed based on only the body position time series data, the activity amount time series data need not be acquired.

Figure 9:
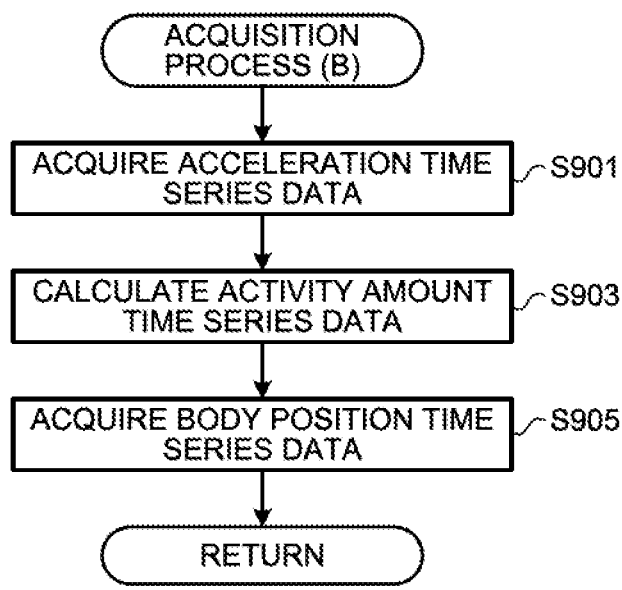
FIG. 9 is a diagram illustrating a flow of an acquisition process (B)

Instead of the acquisition process (A) represented in FIG. 8, an acquisition process (B) illustrated in FIG. 9 may be executed. In the acquisition process (B), only the acceleration time series data is acquired. Accordingly, the sensor device 101 need not calculate amounts of activity. Furthermore, the sensor device 101 need not determine body positions.

FIG. 9 illustrates a flow of the acquisition process (B). The acquisition unit 403 acquires the acceleration time series data via the communication interface device 431 (S901). The analyzing unit 405 calculates activity amount time series data based on the acceleration time series data (S903). A method of calculating amounts of activity accords with related technologies. Furthermore, the analyzing unit 405 calculates body position time series data based on the acceleration time series data (S905). A method of determining body positions accord with related technologies.

When analysis is performed based on only the activity amount time series data, body position time series data need not be calculated. When analysis is performed based on only the body position time series data, activity amount time series data need not be calculated. On ending the acquisition process (B), return to the main process (A) that is the caller process.

In this example, the example where the communication interface device 431 acquires the time series data is represented; however, the network communication device 433 may receive the time series data. The data acquired in the acquisition process (A) or the acquisition process (B) is stored in the first table storing unit 421.

Return to descriptions of FIG. 7. The analyzing unit 405 specifies a getting-into-bed time point and a getting-out-of-bed time point based on the activity amount time series data and/or the body position time series data (S705). A method of specifying a getting-into-bed time point and a getting-out-of-bed time point accords with related technologies. The getting into bed and getting out of bed are recorded in a field for events of the records corresponding to the time points in the first table. When a sensor other than acceleration sensors is used as described above, the analyzing unit 405 may specify a getting-into-bed time point and a getting-out-of-bed time point from all or part of the time series data about heart rates, breathing rates and body motions.

The analyzing unit 405 sets the period from the getting-into-bed time point until the getting-out-of-bed time point as the evaluation period (S707). An evaluation period is an internal parameter that is specified by the dates and times of a start time point and an end time point and is temporarily stored for the analysis process.

The analyzer executes the analysis process (S709). In the analysis process, the state of the subject relating to sleep in each of the three sections obtained by dividing the evaluation period is analyzed to obtain results of evaluation.

Figure 10:
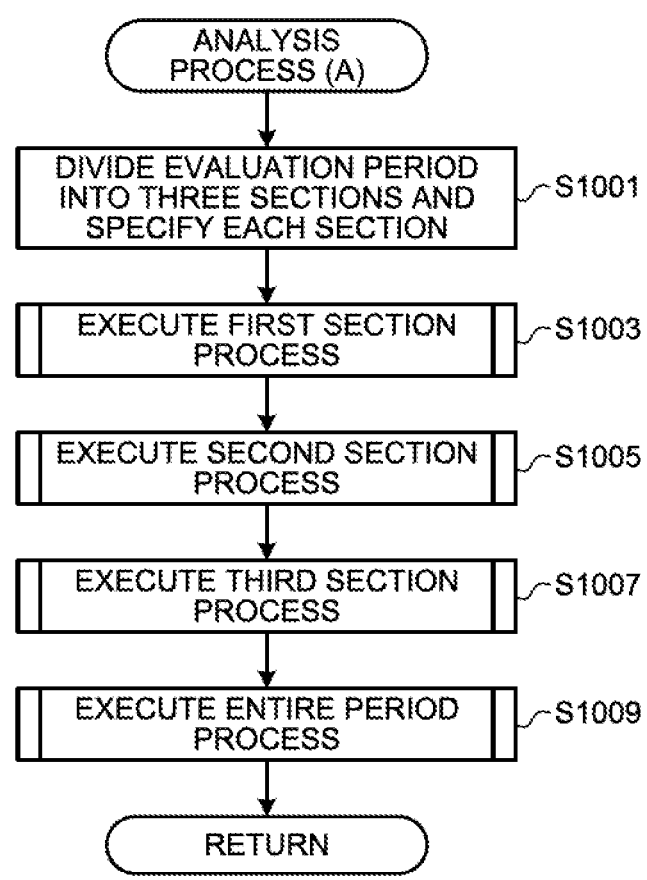
FIG. 10 is a diagram illustrating a flow of an analysis process (A)

In the present embodiment, an analysis process (A) is executed. FIG. 10 illustrates a flow of the analysis process (A). The analyzing unit 405 divides the evaluation period into three sections and specifies each of the sections (S1001). Each of the sections is specified by a start time and an end time of the section. For example, division into three sections having equal lengths may be performed. Alternatively, division into three sections having unequal lengths may be performed. Any of the sections may have a given length. Furthermore, the length of any of the sections may occupy a given ratio of the evaluation period.

The analyzing unit 405 executes a first section process (S1003). In the first section process, analysis on the first section is performed. The first section process will be described below using FIG. 11.

The analyzing unit 405 executes a second section process (S1005). In the second section process, analysis on the second section is performed. In the present embodiment, a second section process (A) is executed. The second section process (A) will be described below using FIG. 12.

The analyzing unit 405 executes a third section process (S1007). In the third section process, analysis on the third section is performed. In the present embodiment, a third section process (A) is executed. The third section process (A) will be described below using FIG. 13.

The analyzing unit 405 executes an entire period process (S1009). In the entire period process, analysis on the entire evaluation period is performed. The entire period process (A) will be described below using FIG. 14. On ending the analysis process, return to the main process (A) that is the caller process.

Figure 11:
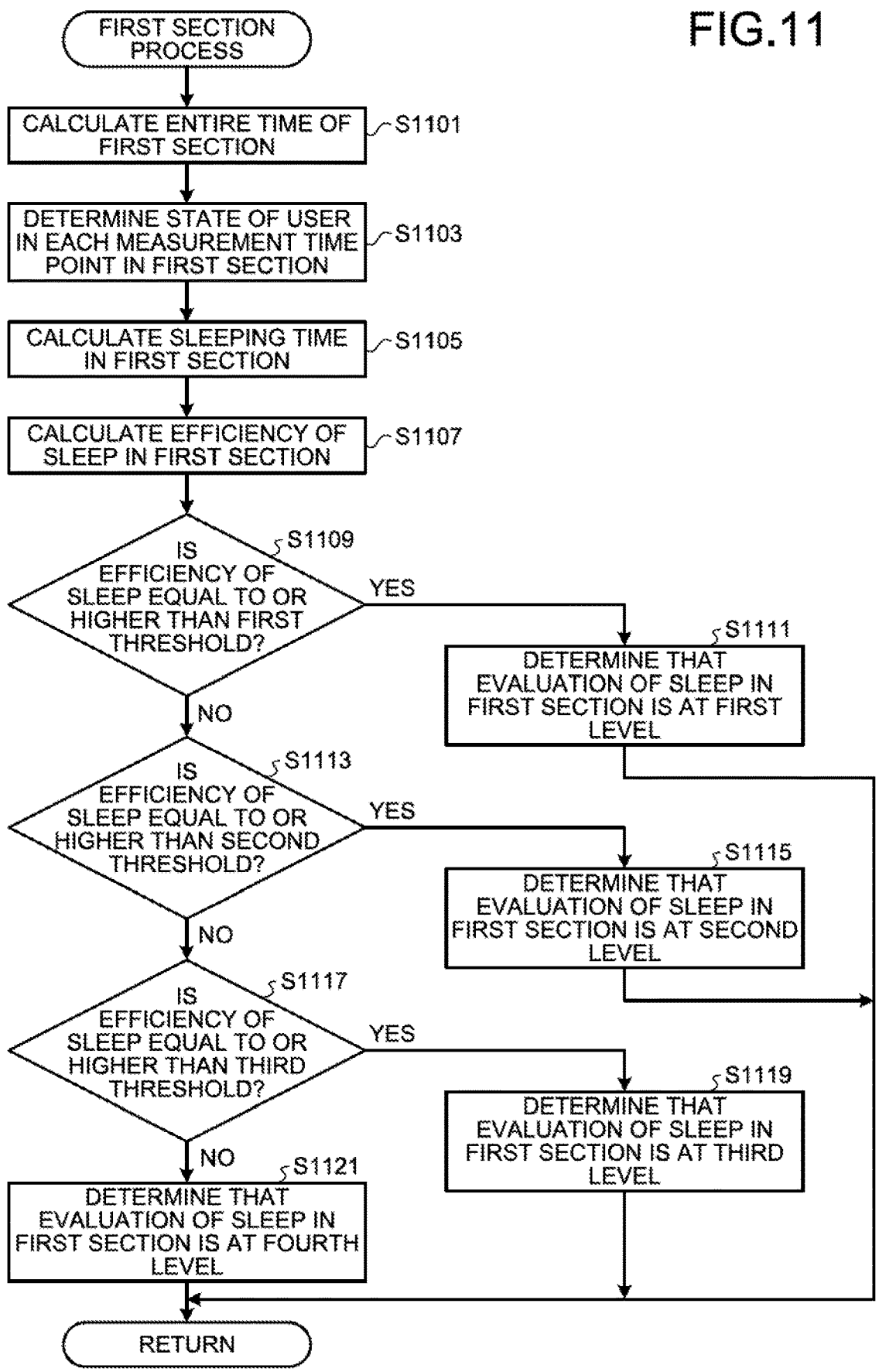
FIG. 11 is a diagram illustrating a flow of a first section process.

FIG. 11 illustrates a flow of the first section process. The analyzing unit 405 calculates an entire time of the first section (S1101). For any of the sections, the entire time of the section is calculated as the difference between the start time and the end time of the section.

The analyzing unit 405 determines a state of the user at each measurement time point in the first section based on the activity amount time series data and/or the body position time series data (S1103). The analyzing unit 405 may determine the state of the user at each measurement time point in the first section from all or part of the time series data about heart rates, breathing rates and body motions. The state of the user is any one of the awake state and the sleep state. The sleep state may be divided into multiple states, such as a light sleep state and a deep sleep state. The states of the user are recorded in the record corresponding to each of the measurement time points in the first table. A method of determining the state of the user accords with related technologies.

The analyzing unit 405 calculates a sleeping time in the first section (S1105). With respect to any section, a sleeping time of the section is calculated by multiplying the number of records corresponding to the sleep state in the section by a measurement interval.

The analyzing unit 405 calculates an efficiency of sleep in the first section (S1107). Specifically, the efficiency of sleep may be calculated by dividing the sleeping time in the first section by the entire time of the first section. For example, the values of the measurement interval corresponding to the first section and each of the items "state of the user" are referred to and the length of accumulated time of measurement intervals with which the sleep state is associated by the length of time of the first section.

The analyzing unit 405 determines whether the efficiency of sleep is equal to or higher than a first threshold (for example, 0.90) (S1109). When it is determined that the efficiency of sleep is equal to or higher than the first threshold, the analyzing unit 405 determines that the evaluation of the sleep in the first section is at the first level (S1111).

On the other hand, when it is determined that the efficiency of sleep is lower than the first threshold, the analyzing unit 405 determines whether the efficiency of sleep is equal to or higher than a second threshold (for example, 0.80) (S1113). When it is determined that the efficiency of sleep is equal to or higher than the second threshold, the analyzing unit 405 determines that the evaluation of the sleep in the first section is at a second level (S1115).

On the other hand, when it is determined that the efficiency of sleep is lower than the second threshold, the analyzing unit 405 determines whether the efficiency of sleep is equal to or higher than a third threshold (for example, 0.70) (S1117). When it is determined that the efficiency of sleep is equal to or higher than the third threshold, the analyzing unit 405 determines that the evaluation of the sleep in the first section is at a third level (S1119).

On the other hand, when it is determined that the efficiency of sleep is lower than the third threshold, the analyzing unit 405 determines that the evaluation of the sleep in the first section is at a fourth level (S1121). On ending the first section process, return to the analysis process (A) that is the caller process.

Figure 12:
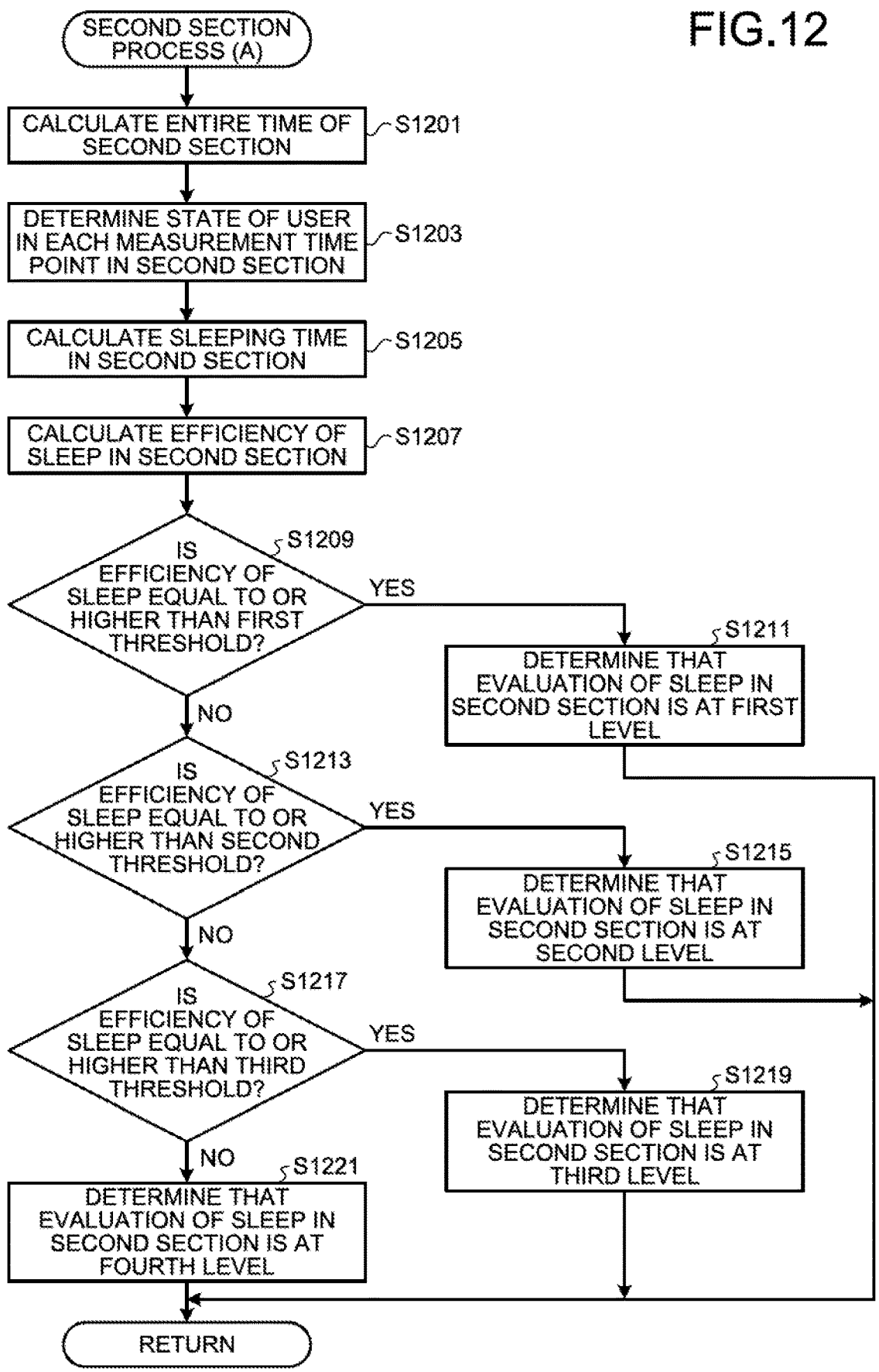
FIG. 12 is a diagram illustrating a flow of a second section process (A)

FIG. 12 illustrates a flow of a second section process (A). In the second section process (A), the same process as the first section process is performed on the second section.

The analyzing unit 405 calculates an entire time of the second section (S1201).

The analyzing unit 405 determines a state of the user at each measurement time point in the second section based on the activity amount time series data and/or the body position time series data (S1203).

The analyzing unit 405 calculates a sleeping time in the second section (S1205).

The analyzing unit 405 calculates an efficiency of sleep in the second section (S1207).

The analyzing unit 405 determines whether the efficiency of sleep is equal to or higher than the first threshold (S1209). When it is determined that the efficiency of sleep is equal to or higher than the first threshold, the analyzing unit 405 determines that the evaluation of the sleep in the second section is at the first level (S1211).

On the other hand, when it is determined that the efficiency of sleep is lower than the first threshold, the analyzing unit 405 determines whether the efficiency of sleep is equal to or higher than the second threshold (S1213). When it is determined that the efficiency of sleep is equal to or higher than the second threshold, the analyzing unit 405 determines that the evaluation of the sleep in the second section is at the second level (S1215).

On the other hand, when it is determined that the efficiency of sleep is lower than the second threshold, the analyzing unit 405 determines whether the efficiency of sleep is equal to or higher than the third threshold (S1217). When it is determined that the efficiency of sleep is equal to or higher than the third threshold, the analyzing unit 405 determines that the evaluation of the sleep in the second section is at the third level (S1219).

On the other hand, when it is determined that the efficiency of sleep is lower than the third threshold, the analyzing unit 405 determines that the evaluation of the sleep in the second section is at the fourth level (S1221). On ending the second section process (A), return to the analysis process (A) that is the caller process.

Figure 13:
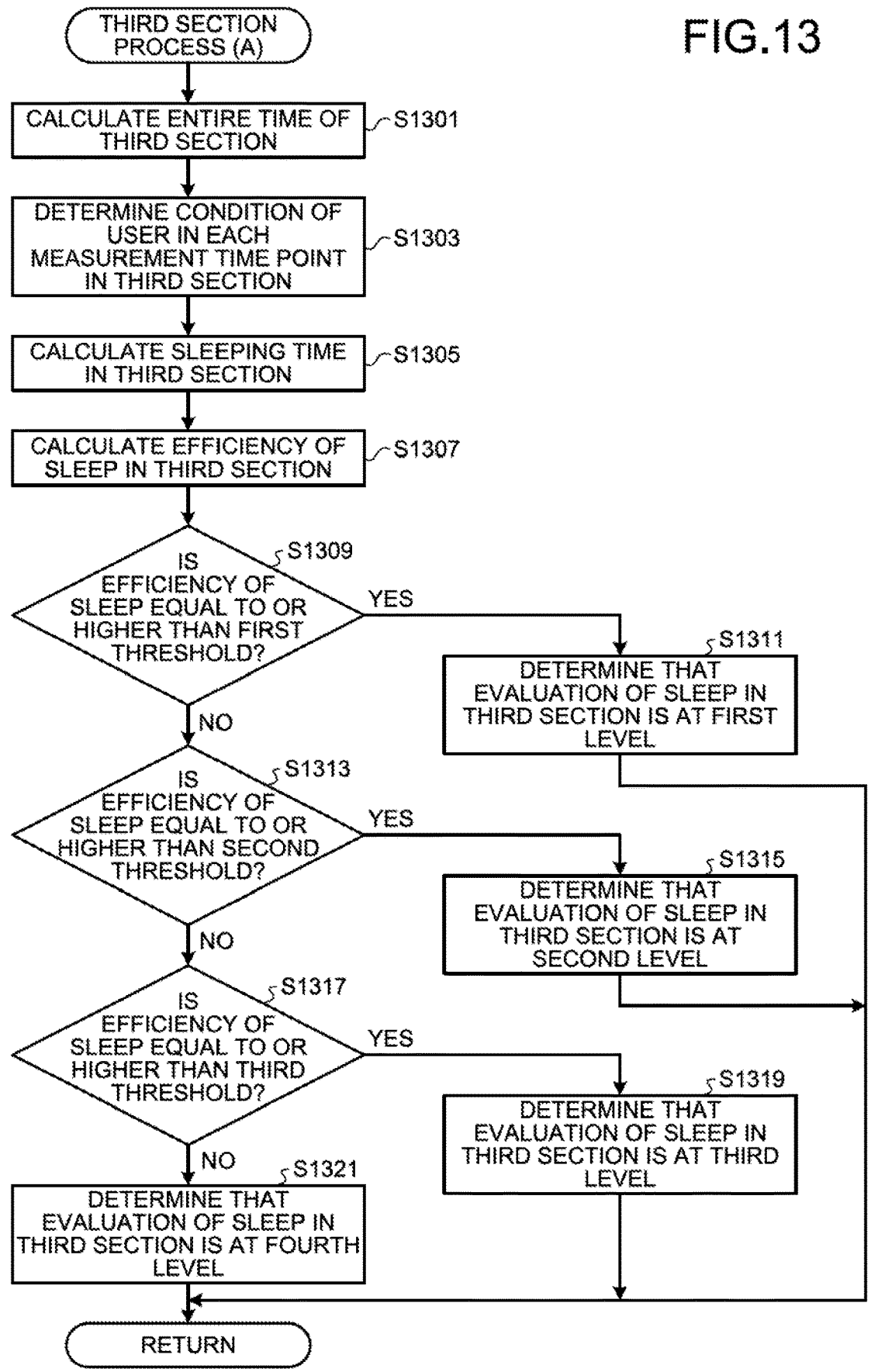
FIG. 13 is a diagram illustrating a flow of a third section process (A)

FIG. 13 illustrates a flow of a third section process (A). In the third section process (A), the same process as the first section process is performed on the third section.

The analyzing unit 405 calculates an entire time of the third section (S1301).

The analyzing unit 405 determines a state of the user at each measurement time point in the third section based on the activity amount time series data and/or the body position time series data (S1303).

The analyzing unit 405 calculates a sleeping time in the third section (S1305).

The analyzing unit 405 calculates an efficiency of sleep in the third section (S1307).

The analyzing unit 405 determines whether the efficiency of sleep is equal to or higher than the first threshold (S1309). When it is determined that the efficiency of sleep is equal to or higher than the first threshold, the analyzing unit 405 determines that the evaluation of the sleep in the third section is at the first level (S1311).

On the other hand, when it is determined that the efficiency of sleep is lower than the first threshold, the analyzing unit 405 determines whether the efficiency of sleep is equal to or higher than the second threshold (S1313). When it is determined that the efficiency of sleep is equal to or higher than the second threshold, the analyzing unit 405 determines that the evaluation of the sleep in the third section is at the second level (S1315).

On the other hand, when it is determined that the efficiency of sleep is lower than the second threshold, the analyzing unit 405 determines whether the efficiency of sleep is equal to or higher than the third threshold (S1317). When it is determined that the efficiency of sleep is equal to or higher than the third threshold, the analyzing unit 405 determines that the evaluation of the sleep in the third section is at the third level (S1319).

On the other hand, when it is determined that the efficiency of sleep is lower than the third threshold, the analyzing unit 405 determines that the evaluation of the sleep in the third section is at the fourth level (S1321). On ending the third section process (A), return to the analysis process (A) that is the caller process.

Figure 14:
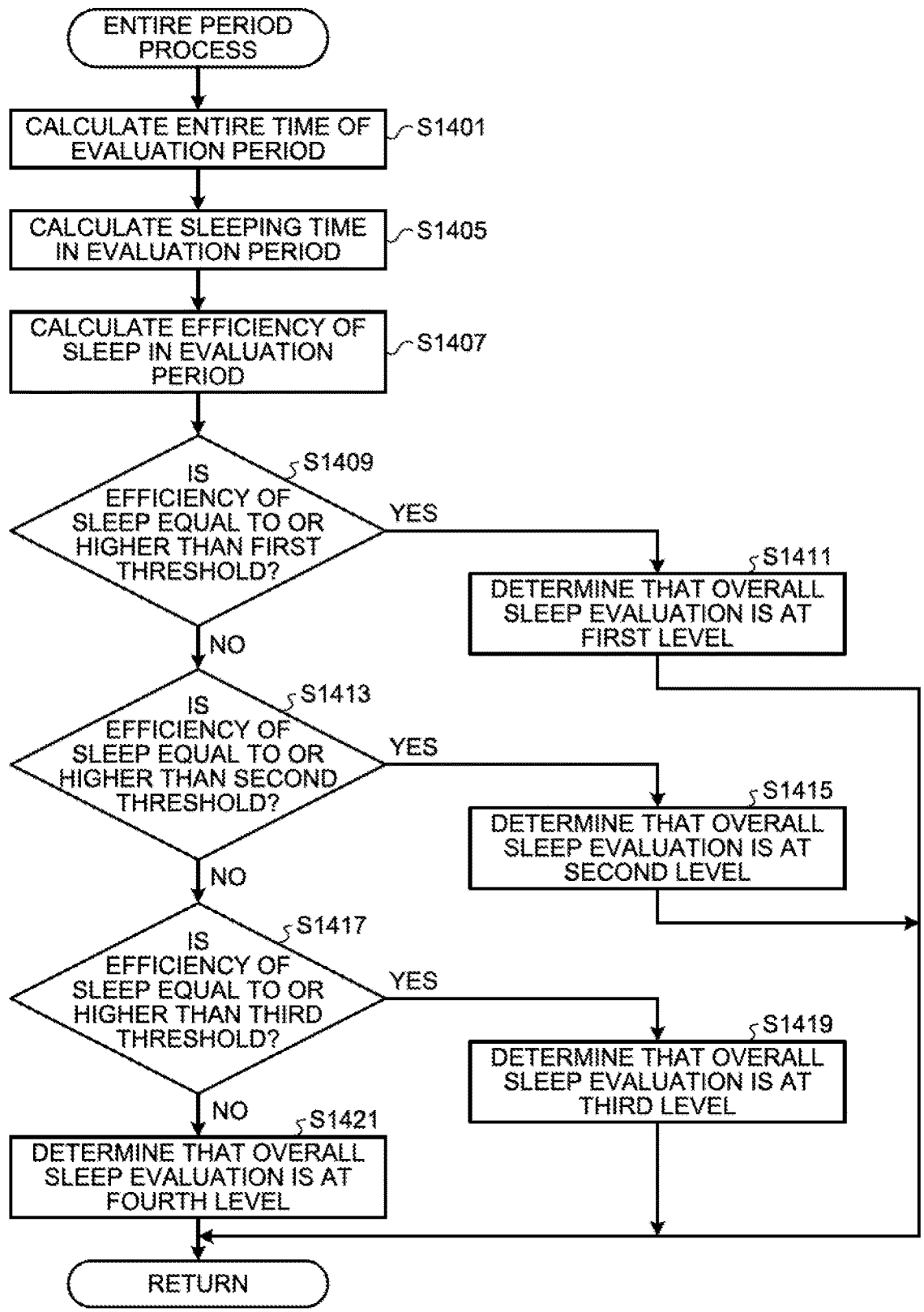
FIG. 14 is a diagram illustrating a flow of an entire period process.

FIG. 14 illustrates a flow of the entire period process (S1401). The analyzing unit 405 calculates a sleeping time in the evaluation period (S1405). The sleeping time in the evaluation period are calculated by multiplying the number of records corresponding to the sleep state in the evaluation period by the measurement interval.

The analyzing unit 405 calculates an efficiency of sleep in the evaluation period (S1407). Specifically, the efficiency of sleep is calculated by dividing the sleeping time in the evaluation period by the entire time of the evaluation period.

The analyzing unit 405 determines whether the efficiency of sleep is equal to or higher than the first threshold (S1409). When it is determined that the efficiency of sleep is equal to or higher than the first threshold, the analyzing unit 405 determines that the overall sleep evaluation is at the first level (S1411).

On the other hand, when it is determined that the efficiency of sleep is lower than the first threshold, the analyzing unit 405 determines whether the efficiency of sleep is equal to or higher than the second threshold (S1413). When it is determined that the efficiency of sleep is equal to or higher than the second threshold, the analyzing unit 405 determines that the overall sleep evaluation is at the second level (S1415).

On the other hand, when it is determined that the efficiency of sleep is lower than the second threshold, the analyzing unit 405 determines whether the efficiency of sleep is equal to or higher than the third threshold (S1417). When it is determined that the efficiency of sleep is equal to or higher than the third threshold, the analyzing unit 405 determines that the overall sleep evaluation is at the third level (S1419).

On the other hand, when it is determined that the efficiency of sleep is lower than the third threshold, the analyzing unit 405 determines that the overall sleep evaluation is at the fourth level (S1421). On ending the entire period process, return to the analysis process (A) that is the caller process.

Return to descriptions of FIG. 7. When the analysis process ends, the display processing unit 407 executes the display process (S711). In the display process, the evaluation screen is displayed.

Figure 15:
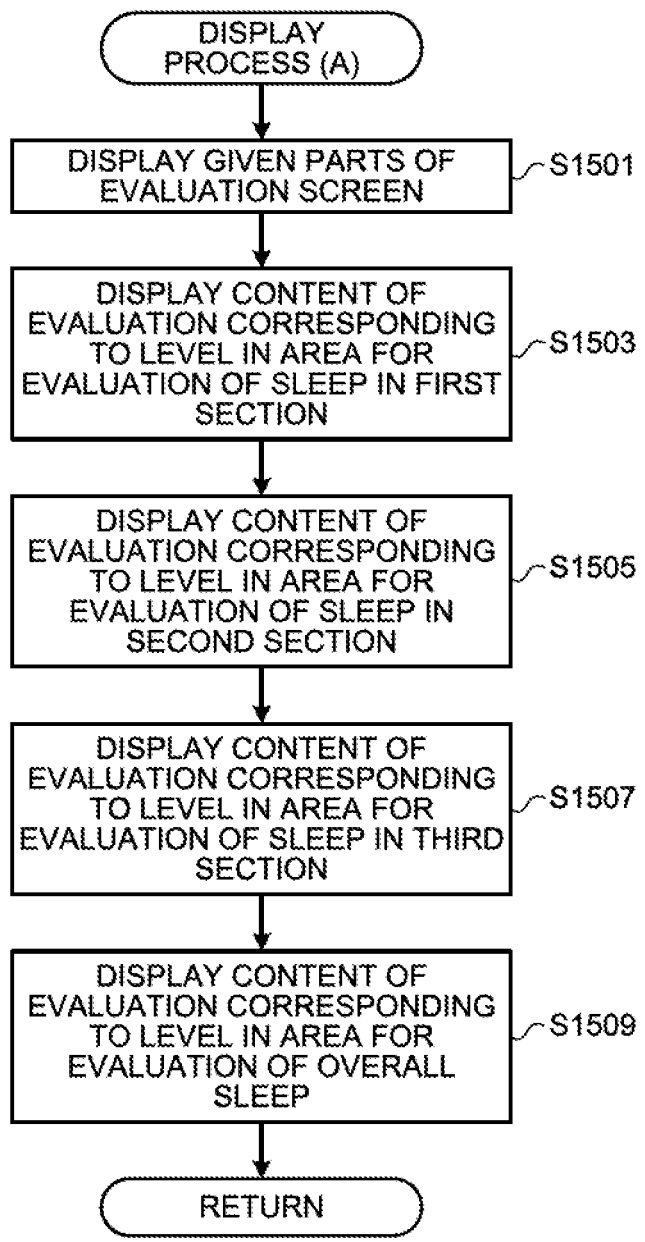
FIG. 15 is a diagram illustrating a flow of a display process (A)

In the present embodiment, a display process (A) is executed. FIG. 15 illustrates a flow of the display process (A). The display processing unit 407 displays a background of the evaluation screen (FIG. 3), a frame and a given character string (S1501). The display processing unit 407 displays the content of evaluation corresponding to the level of the evaluation of the sleep in the first section in the area 301 for evaluation of the sleep in the first section (S1503). The display processing unit 407 displays the content of evaluation corresponding to the level of the evaluation of the sleep in the second section in the area 303 for evaluation of the sleep in the second section (S1505). The display processing unit 407 displays the content of evaluation corresponding to the level of the evaluation of the sleep in the third section in the area 305 for the evaluation of the sleep in the third section (S1507). The display processing unit 407 displays the content of evaluation corresponding to the level of the overall sleep evaluation in the area 307 for the overall sleep evaluation (S1509). When the display process (A) ends, the main process (A) that is the caller process also ends.

The mode of output may be other than display. For example, instead of executing the display process at each of steps S1503, S1505, S1507 and S1509, a process of displaying only the content of evaluation of sleep in a section at a level that meets a given condition may be executed. For example, assume that the level of evaluation of the sleep in the first section represents "slightly bad" and the level of evaluation of the sleep in the second and third sections represents "slightly good". Furthermore, assume that the given condition to determine a subject to be displayed is "equal to or lower than the third level", that is, "slightly bad" or "bad". In this case, "slightly good" may be displayed as the level of evaluation of the sleep in the first section as the result of the display process (A) with evaluation of the sleep in the second and third sections and the entire sleep being not displayed. In the above-described case, display of given parts at step S1501 is display of only parts of the display column about the section that meets the given condition that determines a subject to be displayed. According to the above-described given condition to determine the subject to be displayed, only a section at a level better than the level of the overall sleep evaluation or a section at a level worse than the level of the overall sleep evaluation may be displayed. Furthermore, according to the given condition to determine the subject to be displayed, only a section at the worst level among the first, second and third sections may be displayed. Furthermore, as for a destination of output, for example, the data of the evaluation screen may be transmitted to the user terminal 203. Alternatively, the data of the evaluation screen may be written in a storage medium.

According to the present embodiment, the quality of sleep is known easily by focusing on the onset of sleep, continuity of sleep and waking. For example, it is useful for the manager to estimate the body condition of the subject based on those viewpoints. In many cases where people are dissatisfied with sleep, there is some sort of problem with the state of onset of sleep and the state before getting out of bed. Dividing the sleep time length into the early, middle and late sections enables output of the sleep state and advices with respect to the time band including the early and late sections in which people tend to be dissatisfied and the time band of the middle section in which people tend not to be dissatisfied.

Second Embodiment

The present embodiment illustrates an example where a reference to determine a level of evaluation of sleep differs according to each section. Specifically, a threshold of efficiency of sleep in the late section is smaller than that in the early section. In other words, evaluation of the sleep in the late section tends to be better than that in the early section.

Figure 16:
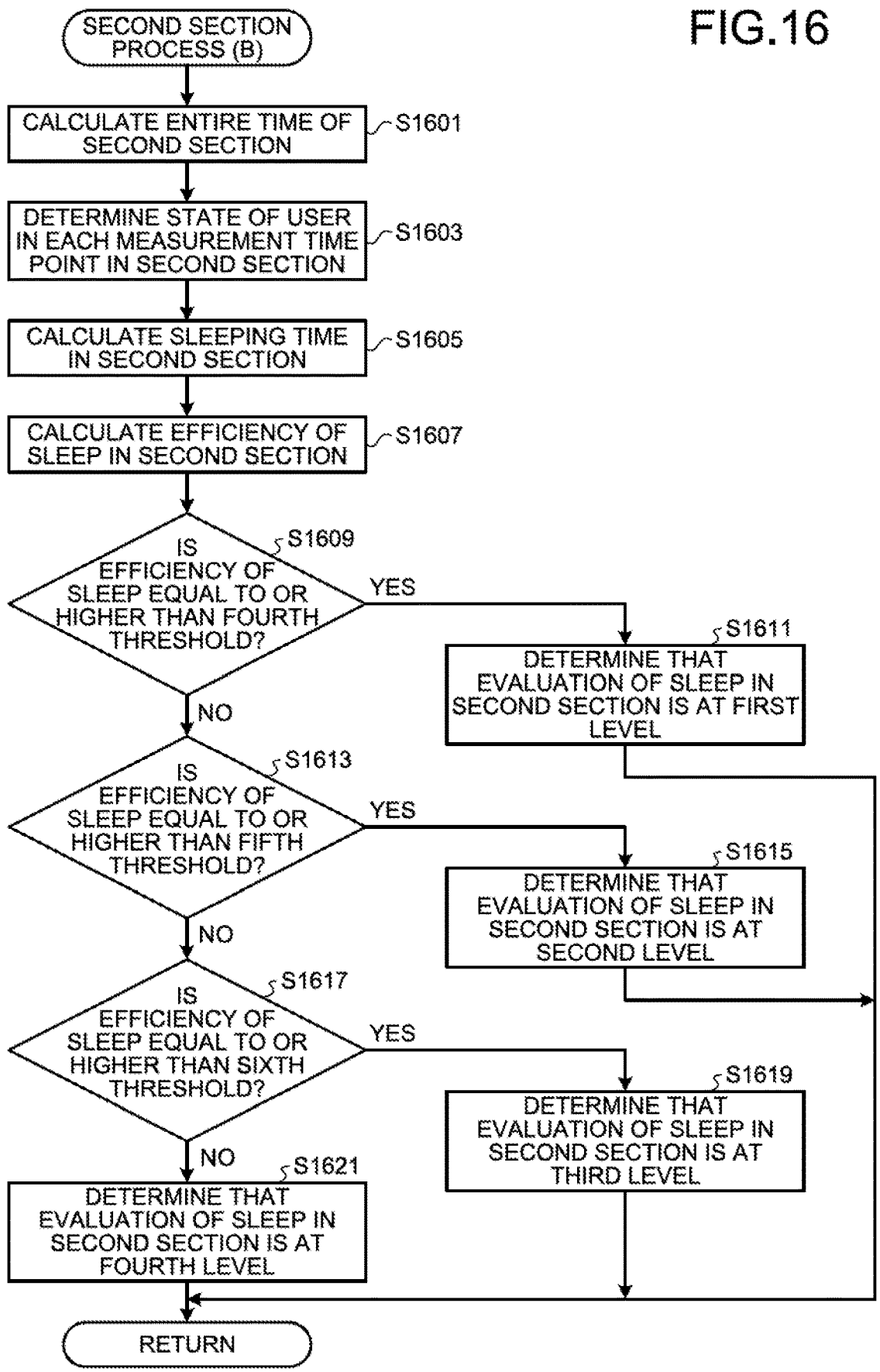
FIG. 16 is a diagram illustrating a flow of a second section process (B)

In the present embodiment, instead of the second section process (A), a second section process (B) is executed. FIG. 16 illustrates a flow of the second section process (B). The processes from S1601 to S1607 are the same as the processes from S1201 to S1207 in the second section process (A).

The analyzing unit 405 determines whether the efficiency of sleep is equal to or higher than a fourth threshold (for example, 0.85) (S1609). The fourth threshold is smaller than the first threshold. When it is determined that the efficiency of sleep is equal to or higher than the fourth threshold, the analyzing unit 405 determines that the evaluation of the sleep in the second section is at the first level (S1611).

On the other hand, when it is determined that the efficiency of sleep is lower than the fourth threshold, the analyzing unit 405 determines whether the efficiency of sleep is equal to or higher than a fifth threshold (for example, 0.75) (S1613). The fifth threshold is smaller than the second threshold. When it is determined that the efficiency of sleep is equal to or higher than the fifth threshold, the analyzing unit 405 determines that the evaluation of the sleep in the second section is at the second level (S1615).

On the other hand, when it is determined that the efficiency of sleep is lower than the fifth threshold, the analyzing unit 405 determines whether the efficiency of sleep is equal to or higher than a sixth threshold (for example, 0.65) (S1617). The sixth threshold is smaller than the third threshold. When it is determined that the efficiency of sleep is equal to or higher than the sixth third threshold, the analyzing unit 405 determines that the evaluation of the sleep in the second section is at the third level (S1619).

On the other hand, when it is determined that the efficiency of sleep is lower than the sixth threshold, the analyzing unit 405 determines that the evaluation of the sleep in the second section is at the fourth level (S1621). On ending the second section process (B), return to the analysis process (A) that is the caller process.

Figure 17:
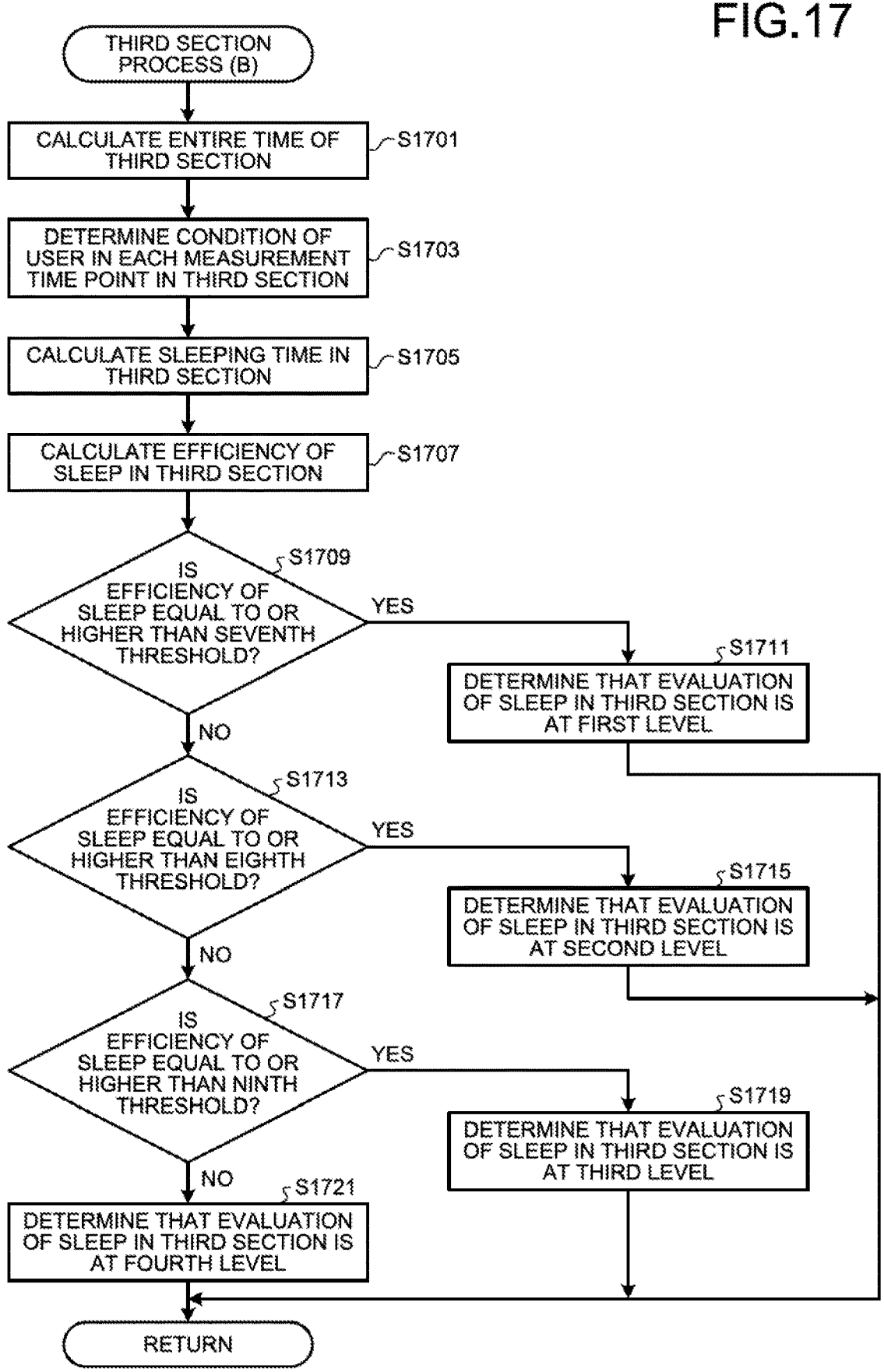
FIG. 17 is a diagram illustrating a flow of a third section process (B)

In the present embodiment, instead of the third section process (A), a third section process (B) is executed. FIG. 17 illustrates a flow of the third section process (B). The processes from 51701 to S1707 are the same as the processes from S1301 to S1307 in the third section process (A).

The analyzing unit 405 determines whether the efficiency of sleep is equal to or higher than a seventh threshold (for example, 0.80) (S1709). The seventh threshold is smaller than the first threshold and the fourth threshold. When it is determined that the efficiency of sleep is equal to or higher than the seventh threshold, the analyzing unit 405 determines that the evaluation of the sleep in the third section is at the first level (S1711).

On the other hand, when it is determined that the efficiency of sleep is lower than the fourth threshold, the analyzing unit 405 determines whether the efficiency of sleep is equal to or higher than an eighth threshold (for example, 0.70) (S1713). The eighth threshold is smaller than the second threshold and the fifth threshold. When it is determined that the efficiency of sleep is equal to or higher than the eighth threshold, the analyzing unit 405 determines that the evaluation of the sleep in the third section is at the second level (S1715).

On the other hand, when it is determined that the efficiency of sleep is lower than the eighth threshold, the analyzing unit 405 determines whether the efficiency of sleep is equal to or higher than a ninth threshold (for example, 0.60) (S1717). The ninth threshold is smaller than the third threshold and the sixth threshold. When it is determined that the efficiency of sleep is equal to or higher than the ninth threshold, the analyzing unit 405 determines that the evaluation of the sleep in the third section is at a third level (S1719).

On the other hand, when it is determined that the efficiency of sleep is lower than the ninth threshold, the analyzing unit 405 determines that the evaluation of the sleep in the third section is at a fourth level (S1721). On ending the third section process (B), return to the analysis process (A) that is the caller process.

Other processes are the same as those of the first embodiment.

The fourth threshold may be equal to the first threshold. The fifth threshold may be equal to the second threshold. The sixth threshold may be equal to the third threshold.

Alternatively, the fourth threshold may be equal to the seventh threshold. The fifth threshold may be equal to the eighth threshold. The sixth threshold may be equal to the ninth threshold.

According to the present embodiment, it is possible to enable a relatively better result of evaluation of the third section than that by analysis on the first section. As the time to get out of bed approaches, human sleep commonly becomes light naturally and thus, even when sleep is taken without problem, the evaluation of a time band close to the time to get out of bed, that is, the time band corresponding to the late period from among the early, middle and late periods of the sleeping time, tends to be worse. Implementing relatively better result of evaluation of the third section than that by analysis on the first section makes it easy to compare the quality of sleep in the late period with the quality of sleep in the early period.

Specifically, it makes it easy to compare the quality of sleep in the late period in which the ratio of the sleep state tends to reduce with the quality of sleep in the early period.

Third Embodiment

In the present embodiment, it makes it easier to determine that it is the sleep state when efficiency of sleep in the late section is calculated than when the efficiency of sleep in the early section is calculated.

In the process at S1607 illustrated in FIG. 16, it makes it easier to determine that it is the sleep state than the case of the process at S1107 illustrated in FIG. 11. For example, increasing the upper limit value of amount of activity serving as a condition to determine that it is the sleep state in the related technology to that larger than that at S1207 makes it easy to determine that it is the sleep state. Alternatively, reducing the lower limit value of duration of time of the same body position serving as a condition to determine that it is the sleep state in the related technology to that smaller than that at S1207 makes it easy easy to determine that it is the sleep state.

Accordingly, the efficiency of sleep in the second section tends to be higher than that by analysis on the first section. Even if the fourth threshold is equal to the first threshold, the fifth threshold is equal to the second threshold and the sixth threshold is equal to the third threshold, the result of evaluation of the second section tends to be relatively better.

Similarly, also in the process at S1707 illustrated in FIG. 17, it makes it easier to determine that it is the sleep state than in the process at S1607 illustrated in FIG. 16.

Accordingly, the efficiency of sleep in the third section tends to be higher than that by analysis on the second section. Even if the seventh threshold is equal to the fourth threshold, the eighth threshold is equal to the fifth threshold and the ninth threshold is equal to the sixth threshold, the result of evaluation of the third section tends to be better.

At least making it easier to determine that it is the sleep state in the process at S1707 illustrated in FIG. 17 than in the process at S1107 illustrated in FIG. 11 tends to make the result of evaluation by analysis on the third section relatively better than that by analysis on the first section.

According to the present embodiment, the quality of sleep in the late period in which sleep tends to be light is easily compared with the quality of sleep in the early period.

Fourth Embodiment

In the present embodiment, the evaluation period stretches from an onset-of-sleep time point to a waking time point.

Figure 18:
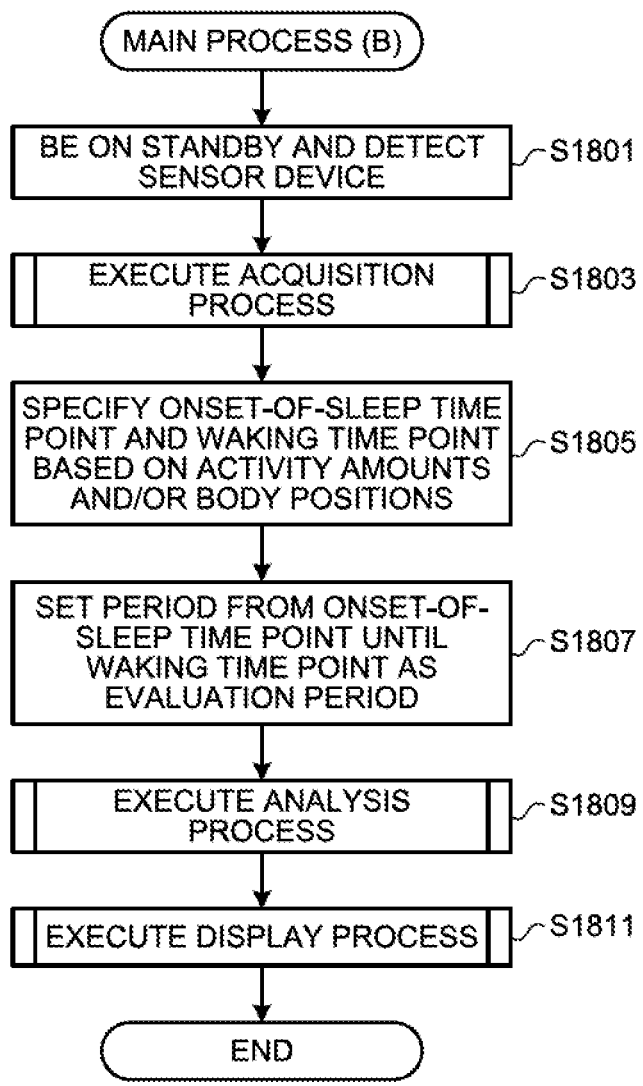
FIG. 18 is a diagram illustrating a flow of a main process (B)

In the present embodiment, instead of the main process (A), a main process (B) is executed. The present embodiment may be applied to any of the first to third embodiments. FIG. 18 illustrates a flow of the main process (B). The processes at step S1801 and S1803 are the same as the processes at S701 and S703 illustrated in FIG. 7.

The analyzing unit 405 specifies the first onset-of-sleep time point after getting into bed and the last waking time point before getting out of bed based on the activity amount time series data and/or the body position time series data (S1805). A method of specifying an onset-of-sleep time point and a waking time point accords with related technologies. The onset of sleep and waking are recorded in the field for events of the records corresponding to the time points in the first table.

The period from the onset-of-sleep time point after the getting into bed until the last waking point before the getting out of bed is set as the evaluation period (S1807).

The processes at S1809 and S1811 are the same as the processes at S709 and S711 illustrated in FIG. 7.

It can be assumed that, even when a person gets into bed, the person is not going to sleep and may be in a lying posture for some reasons. According to the present embodiment, sleep can be evaluated more correctly when an elapsed time that has to be excluded from evaluation is contained in the period after getting into bed until onset of sleep or the period from awaking until getting out of bed.

Fifth Embodiment

In the present embodiment, an evaluation period stretches from a getting-into-bed time point to a waking time point.

Figure 19:
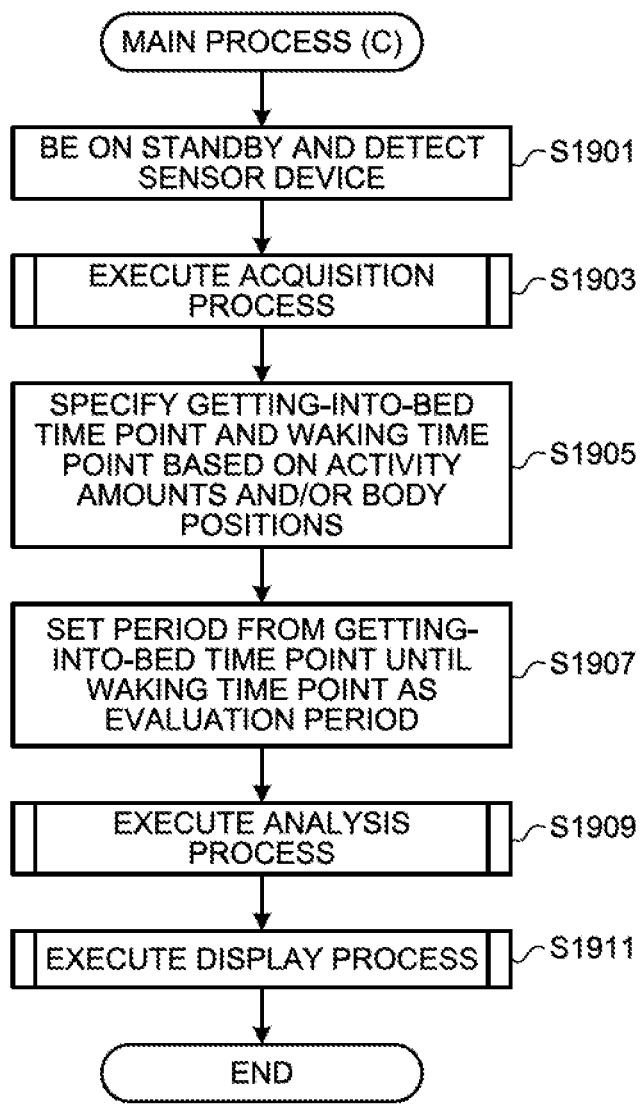
FIG. 19 is a diagram illustrating a flow of a main process (C)

In the present embodiment, instead of the main process (A), a main process (C) is executed. The present embodiment may be applied to any of the first to third embodiments. FIG. 19 illustrates a flow of the main process (C). The processes at S1901 and S1903 are the same as the processes at S701 and S703 illustrated in FIG. 7.

The analyzing unit 405 specifies a getting-into-bed time point and the last waking time point before getting out of bed based on the activity amount time series data and/or the body position time series data (S1905). The getting into bed and waking are recorded in the field for events of the records corresponding to the time points in the first table.

The analyzing unit 405 sets the period from the getting-into-bed time point until the last waking point before the getting out of bed as the evaluation period (S1907).

The processes at S1909 and S1911 are the same as the processes at S709 and S711 illustrated in FIG. 7.

Even when a person wakes up and is not going to sleep, the person may be in a lying posture without getting out of bed for some reasons. According to the present embodiment, it is possible to evaluate sleep more correctly when an elapsed time that has to be excluded from evaluation is contained in the period from waking until getting out of bed.

Sixth Embodiment

In the present embodiment, the evaluation period stretches from a getting-into-bed time point to a getting-out-of-bed time point.

Figure 20:
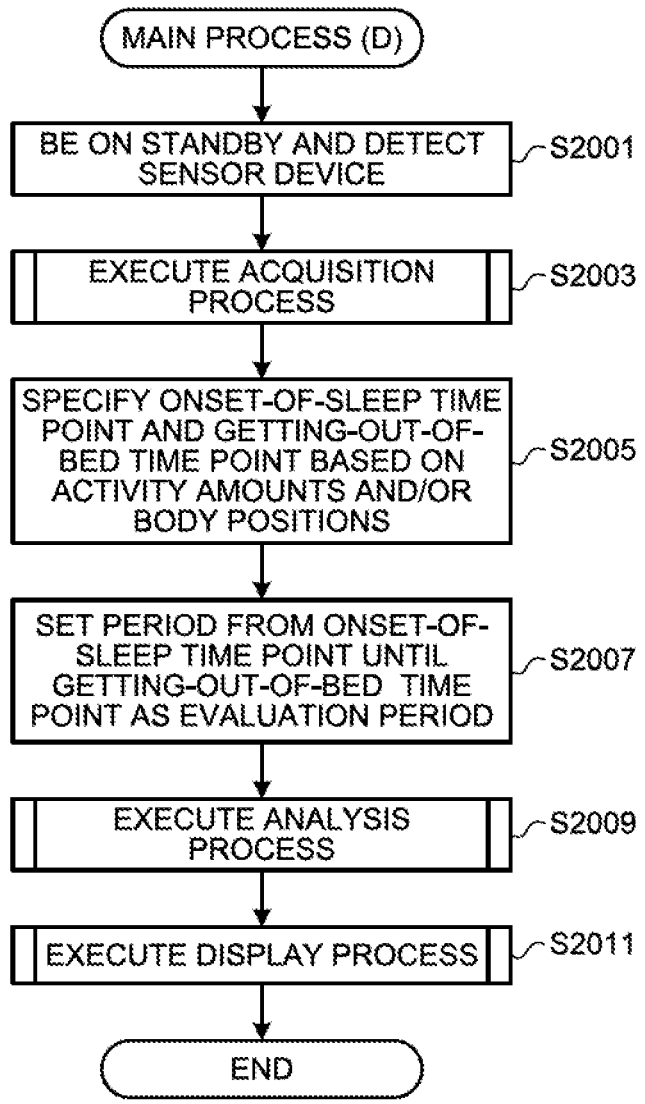
FIG. 20 is a diagram illustrating a flow of a main process (D)

In the present embodiment, instead of the main process (A), a main process (D) is executed. The present embodiment may be applied to any of the first to third embodiments. FIG. 20 illustrates a flow of the main process (D). The processes at S2001 and S2003 are the same as the processes at S701 and S703 illustrated in FIG. 7.

The analyzing unit 405 specifies the first onset-of-sleep time point after getting into bed and a getting-out-of-bed time point (S2005). The onset of sleep and getting out of bed are recorded in the field for events of the records corresponding to the time points in the first table.

The analyzing unit 405 sets the period from the first onset-of-sleep time point after the getting into bed until the getting-out-of-bed time point as the evaluation period (S2007).

The processes at S2009 and S2001 are the same as the processes at S709 and S711 illustrated in FIG. 7.

Even when a person is in bed, it can be assumed that the person is not going to sleep and is in a lying posture for some reasons. According to the present embodiment, it is possible to evaluate sleep more correctly when an elapsed time that has to be excluded from evaluation is contained in the period after getting into bed until onset of sleep.

Seventh Embodiment

In the present embodiment, when the length of an evaluation period exceeds a reference value, the evaluation period is divided into five sections.

FIG. 21 illustrates an exemplary evaluation screen in the seventh embodiment. As in the case according to FIG. 3, content of evaluation of the quality of sleep of the user is represented on the evaluation screen. Specifically, in addition to the content of the entire evaluation, the content of evaluation of each of five sections divided from the evaluation period is represented. In the area 301 for evaluation of the sleep in a first section, the content of evaluation of the first section, that is, a period relating to onset of sleep, is displayed. In the area 303 for evaluation of the sleep in a second section, the content of evaluation of the second section is displayed. In the area 305 for evaluation of the sleep in a third section, content of evaluation of the third section, that is, a middle section, is displayed. The third section corresponds to a period that relates to continuity of sleep. In an area 2101 for evaluation of the sleep in a fourth section, the content of evaluation of the fourth section is displayed. In an area 2103 for evaluation of the sleep in a fifth section, the content of evaluation of the fifth section, that is, a period relating to waking, is displayed. In the area 307 for overall sleep evaluation, the content of evaluation of the entire evaluation period is displayed.

Figure 22:
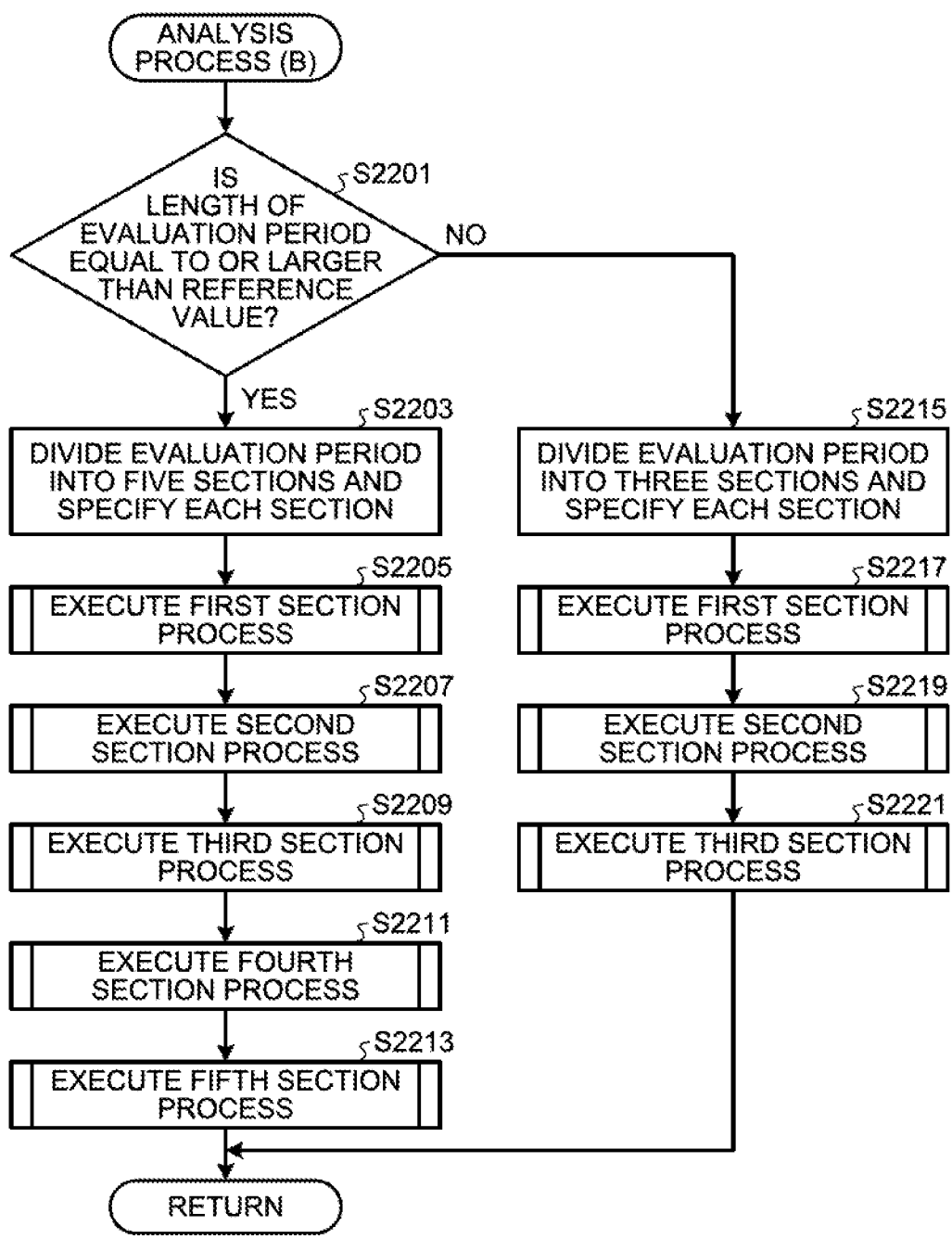
FIG. 22 is a diagram illustrating a flow of an analysis process (B)

In the present embodiment, any one of the main processes (A) to (D) may be executed. Instead of the analysis process (A), an analysis process (B) is executed. FIG. 22 illustrates a flow of the analysis process (B). The analyzing unit 405 determines whether the length of the evaluation period is equal to or larger than a reference value (S2201). When it is determined that the length of the evaluation period is equal to or larger than the reference value (S2201: Yes route), the analyzing unit 405 divides the evaluation period into five sections and specifies each of the sections (S2203). Each of the sections is specified by a start time and an end time of the section. For example, the evaluation period may be divided into five sections having equal lengths. Alternatively, division into into five sections having unequal lengths may be performed. Any of the sections may have a given length. Furthermore, the length of any of the sections may occupy a given ratio of the evaluation period.

The analyzing unit 405 executes the first section process (S2205). The analyzing unit 405 executes the second section process (S2207). The analyzing unit 405 executes the third section process (S2209).

The analyzing unit 405 executes a fourth section process (S2211). In the fourth section process, analysis on the fourth section is performed. The fourth section process will be described below using FIG. 23.

The analyzing unit 405 executes a fifth section process (S2213). In the fifth section process, analysis on the fifth section is performed. The fifth section process will be described below using FIG. 24. On ending the analysis process (B), return to the main process that is the caller process.

When it is determined that the length of the evaluation period is not equal to or larger that the reference value (S2201: No route), the analyzing unit 405 divides the evaluation period into three sections and specifies each of the sections (S2215). The analyzing unit 405 executes the first section process (S2217). The analyzing unit 405 executes the second section process (S2219). The analyzing unit 405 executes the third section process (S2221). On ending the analysis process (B), return to the main process that is the caller process.

Figure 23:
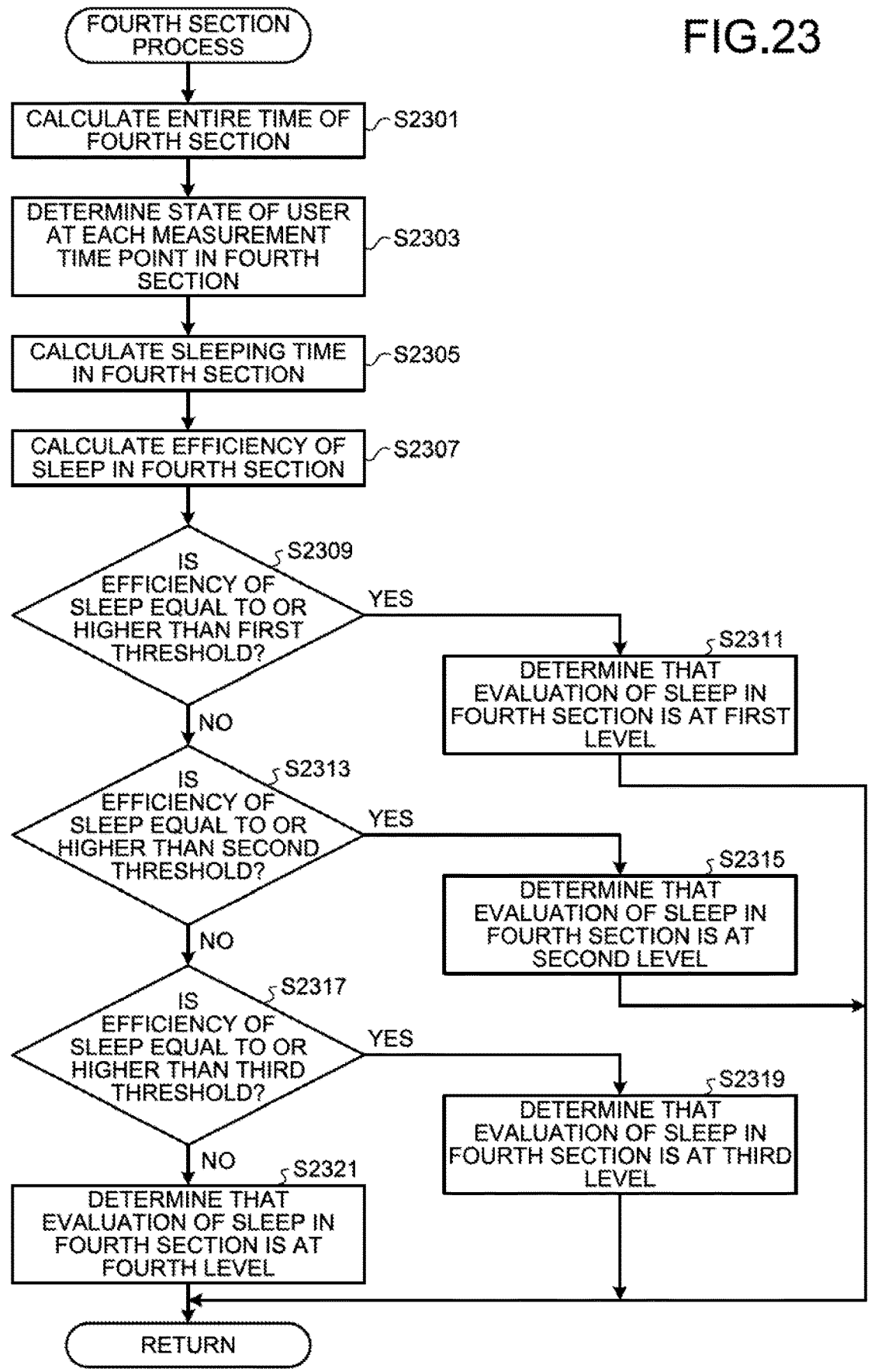
FIG. 23 is a diagram illustrating a fourth section process.

FIG. 23 illustrates a flow of the fourth section process. In the fourth section process, the same process as the first section process is performed on the fourth section.

The analyzing unit 405 calculates an entire time of the fourth section (S2301).

The analyzing unit 405 determines a state of the user at each measurement time point in the fourth section based on the activity amount time series data and/or the body position time series data (S2303).

The analyzing unit 405 calculates a sleeping time in the fourth section (S2305).

The analyzing unit 405 calculates an efficiency of sleep in the fourth section (S2307).

The analyzing unit 405 determines whether the efficiency of sleep is equal to or higher than the first threshold (S2309). When it is determined that the efficiency of sleep is equal to or higher than the first threshold, the analyzing unit 405 determines that the evaluation of the sleep in the fourth section is at the first level (S2311).

On the other hand, when it is determined that the efficiency of sleep is lower than the first threshold, the analyzing unit 405 determines whether the efficiency of sleep is equal to or higher than the second threshold (S2313). When it is determined that the efficiency of sleep is equal to or higher than the second threshold, the analyzing unit 405 determines that the evaluation of the sleep in the fourth section is at the second level (S2315).

On the other hand, when it is determined that the efficiency of sleep is lower than the second threshold, the analyzing unit 405 determines whether the efficiency of sleep is equal to or higher than the third threshold (S2317). When it is determined that the efficiency of sleep is equal to or higher than the third threshold, the analyzing unit 405 determines that the evaluation of the sleep in the fourth section is at the third level (S2319).

On the other hand, when it is determined that the efficiency of sleep is lower than the third threshold, the analyzing unit 405 determines that the evaluation of the sleep in the fourth section is at the fourth level (S2321). On ending the fourth section process, return to the analysis process (B) that is the caller process.

Figure 24:
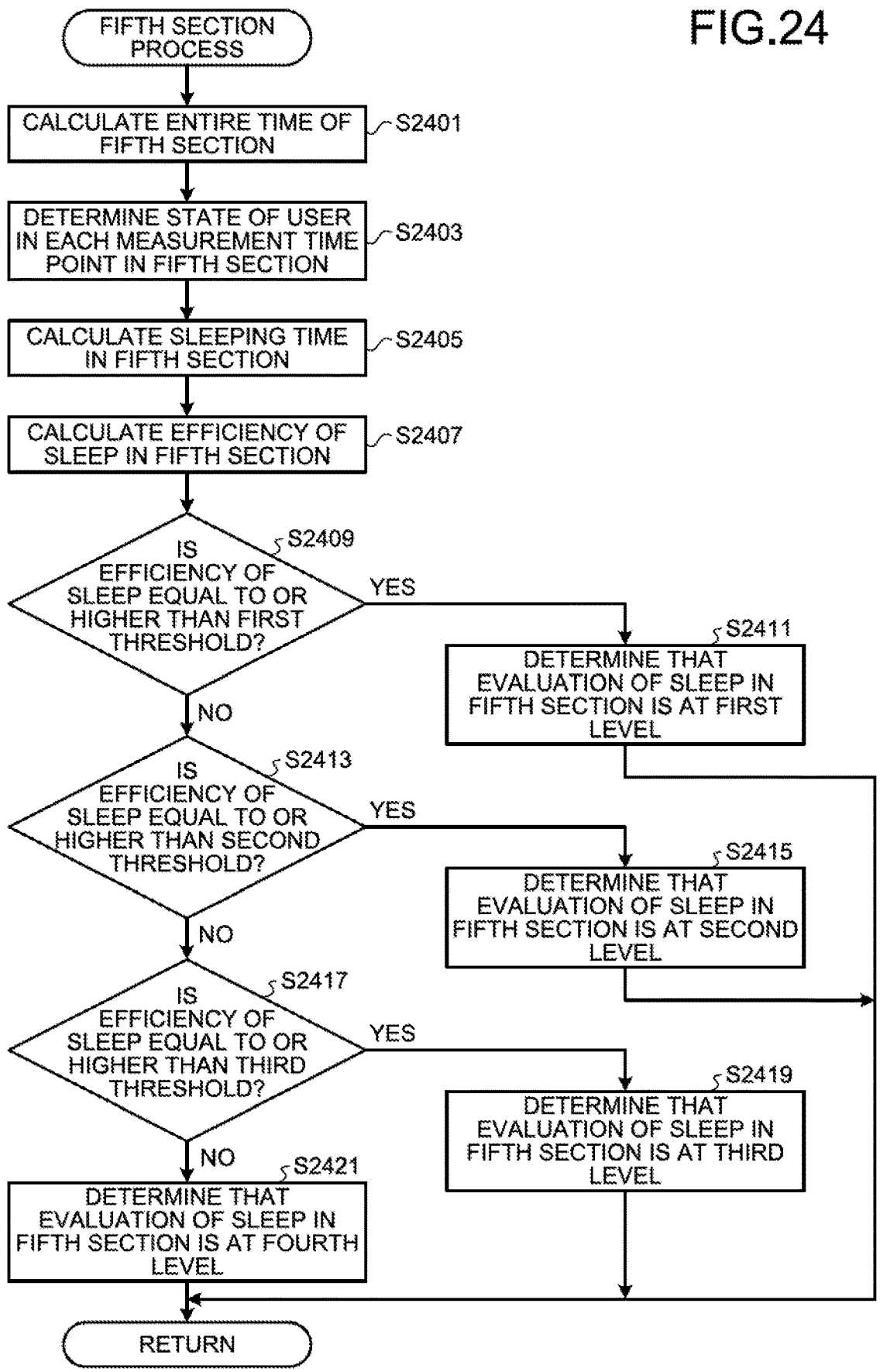
FIG. 24 is a diagram illustrating a fifth section process.

FIG. 24 illustrates a flow of the fifth section process (B). In the fifth section process (A), a process similar to the first section process is performed on the fifth section.

The analyzing unit 405 calculates an entire time of the fifth section (S2401).

The analyzing unit 405 determines a state of the user at each measurement time point in the fifth section based on the activity amount time series data and/or the body position time series data (S2403).

The analyzing unit 405 calculates a sleeping time in the fifth section (S2405).

The analyzing unit 405 calculates an efficiency of sleep in the fifth section (S2407).

The analyzing unit 405 determines whether the efficiency of sleep is equal to or higher than the first threshold (S2409). When it is determined that the efficiency of sleep is equal to or higher than the first threshold, the analyzing unit 405 determines that the evaluation of the sleep in the fifth section is at the first level (S2411).

On the other hand, when it is determined that the efficiency of sleep is lower than the first threshold, the analyzing unit 405 determines whether the efficiency of sleep is equal to or higher than the second threshold (S2413). When it is determined that the efficiency of sleep is equal to or higher than the second threshold, the analyzing unit 405 determines that the evaluation of the sleep in the fifth section is at the second level (S2415).

On the other hand, when it is determined that the efficiency of sleep is lower than the second threshold, the analyzing unit 405 determines whether the efficiency of sleep is equal to or higher than the third threshold (S2417). When it is determined that the efficiency of sleep is equal to or higher than the third threshold, the analyzing unit 405 determines that the evaluation of the sleep in the fifth section is at the third level (S2419).

On the other hand, when it is determined that the efficiency of sleep is lower than the third threshold, the analyzing unit 405 determines that the evaluation of the sleep in the fifth section is at the fourth level (S2421). On ending the fifth section process, return to the analysis process (B) that is the caller process.

Figure 25:
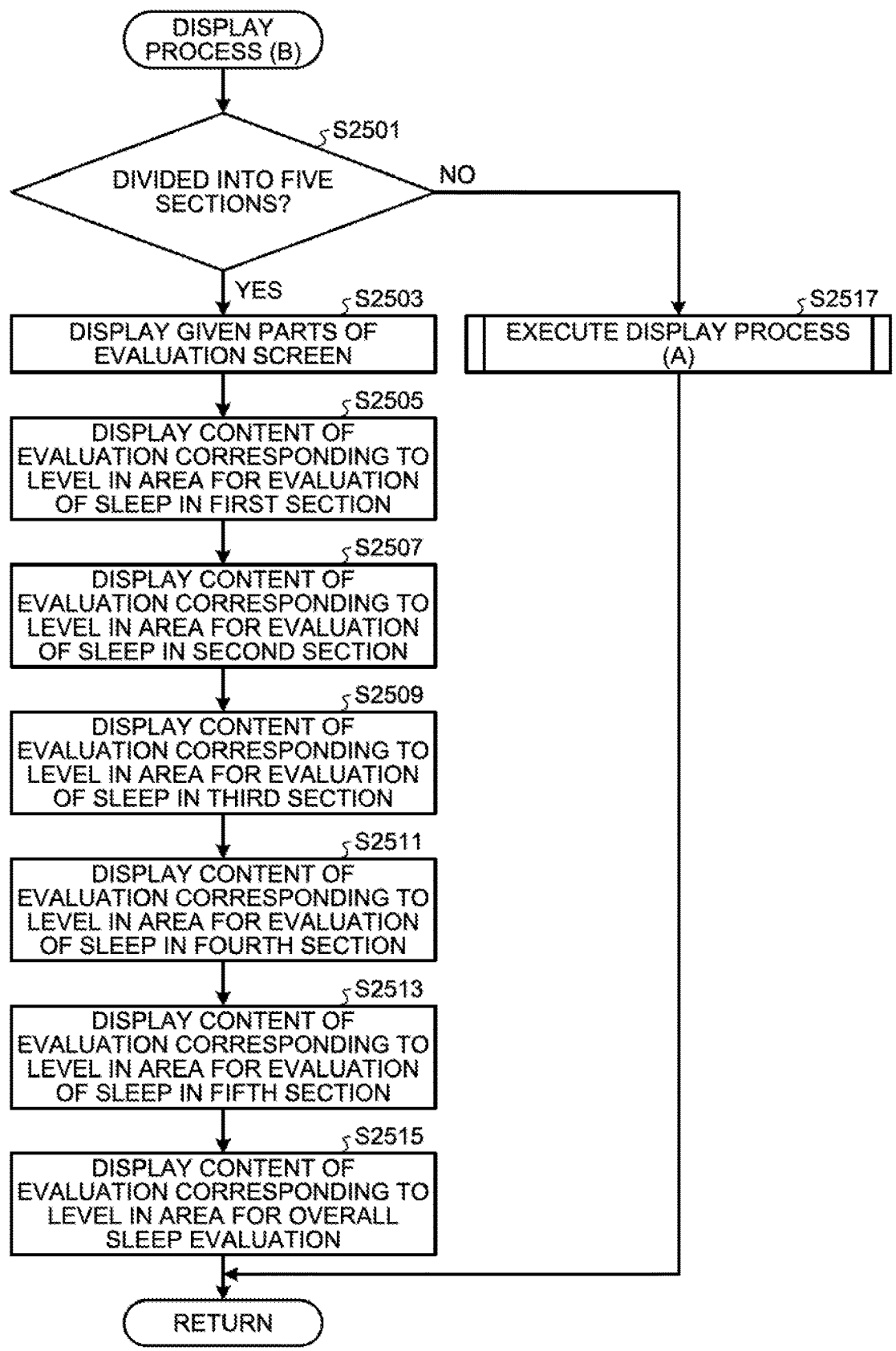
FIG. 25 is a diagram illustrating a flow of a display process (B)

Instead of the display process (A), a display process (B) is executed. FIG. 25 illustrates a flow of the display process (B). The display processing unit 407 determines whether the evaluation period is divided into five sections in the analysis process (B) (S2501).

When it is determined that the evaluation period is divided into five sections, the display processing unit 407 displays a background of the evaluation screen (FIG. 21), a frame and a given character string (S2503). The display processing unit 407 displays the content of evaluation corresponding to the level of the evaluation of the sleep in the first section in the area 301 for evaluation of the sleep in the first section (S2505). The display processing unit 407 displays the content of evaluation corresponding to the level of the evaluation of the sleep in the second section in the area 303 for evaluation of the sleep in the second section (S2507). The display processing unit 407 displays the content of evaluation corresponding to the level of the evaluation of the sleep in the third section in the area 305 for the evaluation of the sleep in the third section (S2509). The display processing unit 407 displays the content of evaluation corresponding to the level of the evaluation of the sleep in the fourth section in the area 2101 for the evaluation of the sleep in the fourth section (S2511). The display processing unit 407 displays the content of evaluation corresponding to the level of the evaluation of the sleep in the fifth section in the area 2103 for the evaluation of the sleep in the fifth section (S2513). The display processing unit 407 displays the content of evaluation corresponding to the level of the overall sleep evaluation in the area 307 for the overall sleep evaluation (S2515). On ending the display process (B), also end the main process that is the caller process.

At S2501 in FIG. 25, when it is determined that the evaluation period is not divided into five sections, the display processing unit 407 executes the display process (A) (S2517). On ending the display process (B), also end the main process that is the caller process.

In the display process (B), as described for the display process (A), instead of executing the display process on each of the first to fifth sections, a process of displaying only the content of evaluation of sleep in a section at a level that meets a given condition may be executed. According to the given condition to determine the subject to be displayed, only a section at a level better than the level of the overall sleep evaluation or a section at a level worse than the level of the overall sleep evaluation may be displayed. Furthermore, according to the given condition to determine the subject to be displayed, only a section at the worst level among the first to fifth sections may be displayed. The second or third embodiment may be applied to the present embodiment.

According to the present embodiment, even when the subject sleeps long, it is possible to evaluate the time of onset of sleep, the middle time and the time of waking.

The embodiments of the present invention have been described above; however, the present invention is not limited thereto. For example, the above-described functional block configuration does not necessarily match the program module configuration.

The configurations of the respective storage areas described above are an example only and the configurations are not necessarily the above-described ones. In the process flows, the turns of processes may be switched or multiple processes may be executed in parallel as long as the processing results do not change.

The above-described information processing device 201 is a computer device. As illustrated in FIG. 26, a memory 2501, a central processing unit (CPU) 2503, a hard disk drive (HDD) 2505, a display controller 2507 that is connected to a display device 2509, a drive device 2513 for a removable disk 2511, an input device 2515 and a communication controller 2517 for connection to a network are connected via a bus 2519. An operating system (OS) and an application program for performing the processes in the embodiments are stored in the HDD 2505 and, when executed by the CPU 2503, are read from the HDD 2505 into the memory 2501. The CPU 2503 controls the display controller 2507, the communication controller 2517 and the drive device 2513 to cause them to perform given operations according to the content of processes of the application program. The data being processed is stored mainly in the memory 2501. Alternatively, the data may be stored in the HDD 2505. In the embodiments of the present invention, the application programs for performing the above-described processes are stored in the computer-readable removable disk 2511 and distributed and then are installed from the drive device 2513 into the HDD 2505. The application program may be installed in the HDD 2505 via a network, such as the Internet, and the communication controller 2517. Such a computer device realizes the various functions like those described above in a way that hardware, such as the CPU 2503 and the memory 2501 described above, and programs, such as the OS and the application program, organically cooperate.

The above-described embodiments of the invention are summarized as follows.

An information processing device according to an embodiment includes (A) an acquisition unit configured to acquire time series data relating to acceleration, amounts of activity of a subject whose sleep is to be evaluated, or body positions of the subject that are measured by a sensor device that the subject wears, or any combination thereof; (B) an analyzer configured to analyze a state of the subject that relates to sleep in each of three sections obtained by dividing an evaluation period from a getting-into-bed time point or the first onset-of-sleep time point after getting into bed that is specified by the time-series data until a getting-out-of-bed time point or the last waking time point before getting out of bed to obtain a result of evaluation; and (C) an output processing unit configured to output the result of evaluation in a state where which one of the sections the result is of is identifiable.

Accordingly, the quality of sleep is known easily by focusing on onset of sleep, continuity of sleep and waking.

The analyzer may be further configured to perform analysis by which the result of evaluation of the last section from among the sections tends to be better than that by analysis on the first section.

Accordingly, the quality of sleep in the late period on which evaluation tends to be worse is compared easily with the quality of sleep in the early period.

The analyzer may be further configured to determine a level of evaluation based on an efficiency of sleep in each of the sections and use, as a first reference to determine the level of evaluation of the last section, a value smaller than a second reference to determine the level of evaluation of the first section.

Accordingly, the quality of sleep in the late period where the ratio of the sleep state tends to decrease is easily compared with the quality of sleep in the early period.

The analyzer may be further configured to determine a level of evaluation based on an efficiency of sleep in each of the sections and make it easier to determine that it is a sleep state when calculating the efficiency of sleep in the last section than when calculating the efficiency of sleep in the first section.

Accordingly, the quality of sleep in the late period where sleep tends to be light is compared easily with the quality of sleep in the early period.

The analyzer may be further configured to, when a length of the evaluation period exceeds a reference value, analyze the state of the subject that relates to sleep in each of five sections obtained by dividing the evaluation period to obtain the result of evaluation.

Accordingly, even when the subject sleeps long, the time of onset of sleep, the middle time, and the time of waking can be evaluated.

A program for causing a computer to perform the processes performed by the above-described information processing device can be created, and the program may be stored in a computer-readable storage medium or a storage device, such as a flexible disk, a CD-ROM, a magneto-optical disk, a semiconductor memory or a hard disk. Note that, generally, intermediate results of processes are stored temporarily in a storage device, such as a main memory.

In one aspect, it is possible to output a result of evaluation from which the quality of sleep is known easily.

All examples and conditional language provided herein are intended for the pedagogical purposes of aiding the reader in understanding the invention and the concepts contributed by the inventors to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. An information processing device comprising:
a processor configured to:
acquire time series data relating to at least one of acceleration, amounts of activity of a subject whose sleep is to be evaluated, and body positions of the subject, the time series data being measured by a sensor device that the subject wears;
obtain a result of evaluation by analyzing a state of the subject that relates to sleep in each of three sections which are obtained by dividing an evaluation period from a getting-into-bed time point or a first onset-of-sleep time point after getting into bed that is specified by the time-series data until a getting-out-of-bed time point or a last waking time point before getting out of bed, the three sections including a first section that is an onset-of-sleep time period, a second section that is a continuity of sleep time period, and a third section that is a waking time period, the analyzing including determining an efficiency of sleep which is a sleeping time in a respective one of the three sections divided by an entire time of the respective one of the three sections,
wherein the processor is further configured to perform the analyzing by which the result of evaluation of the first section is obtained by comparing the efficiency of sleep for the first section with a first threshold and by which the result of evaluation of the third section is obtained by comparing the efficiency of sleep for the third section with a second threshold that is smaller than the first threshold; and
output the result of evaluation to a display, the display providing three areas respectively showing the result of evaluation for each of the three sections and a fourth area showing the result of evaluation for the entire evaluation period.

2. The information processing device according to claim 1, wherein the processor is further configured to, when a length of the evaluation period exceeds a reference value, analyze the state of the subject that relates to sleep in each of five sections obtained by dividing the evaluation period.

3. An information processing method executed by a processor, the information processing method comprising:
acquiring time series data relating to at least one of acceleration, amounts of activity of a subject whose sleep is to be evaluated, and body positions of the subject, the time series data being measured by a sensor device that the subject wears;
obtaining a result of evaluation by analyzing a state of the subject that relates to sleep in each of three sections which are obtained by dividing an evaluation period from a getting-into-bed time point or a first onset-of-sleep time point after getting into bed that is specified by the time-series data until a getting-out-of-bed time point or a last waking time point before getting out of bed, the three sections including a first section that is an onset-of-sleep time period, a second section that is a continuity of sleep time period, and a third section that is a waking time period, the analyzing including determining an efficiency of sleep, which is a sleeping time in a respective one of the three sections divided by an entire time of the respective one of the three sections,
wherein the analyzing further includes comparing the efficiency of sleep for the first section with a first threshold and comparing the efficiency of sleep for the third section with a second threshold that is smaller than the first threshold; and
outputting the result of evaluation to a display, the display providing three areas respectively showing the result of evaluation for each of the three sections and a fourth area showing the result of evaluation for the entire evaluation period.

4. A non-transitory computer-readable recording medium storing therein an information processing program that causes a computer to execute a process, the process comprising:
acquiring time series data relating to at least one of acceleration, amounts of activity of a subject whose sleep is to be evaluated, and body positions of the subject, the time series data being measured by a sensor device that the subject wears;
obtaining a result of evaluation by analyzing a state of the subject that relates to sleep in each of three sections which are obtained by dividing an evaluation period from a getting-into-bed time point or a first onset-of-sleep time point after getting into bed that is specified by the time-series data until a getting-out-of-bed time point or a last waking time point before getting out of bed, the three sections including a first section that is an onset-of-sleep time period, a second section that is a continuity of sleep time period, and a third section that is a waking time period, the analyzing including determining an efficiency of sleep, which is a sleeping time in a respective one of the three sections divided by an entire time of the respective one of the three sections,
wherein the analyzing further includes comparing the efficiency of sleep for the first section with a first threshold and comparing the efficiency of sleep for the third section with a second threshold that is smaller than the first threshold; and
outputting the result of evaluation to a display, the display providing three areas respectively showing the result of evaluation for each of the three sections and a fourth area showing the result of evaluation for the entire evaluation period.

* * * * *